US009930899B2

(12) United States Patent
Van Den Brink et al.

(10) Patent No.: US 9,930,899 B2
(45) Date of Patent: Apr. 3, 2018

(54) VARIANTS OF CHYMOSIN WITH IMPROVED MILK-CLOTTING PROPERTIES

(71) Applicant: Chr. Hansen A/S, Hoersholm (DK)

(72) Inventors: Johannes Maarten Van Den Brink, Herlev (DK); Martin Lund, Copenhagen Ø (DK); Jonas Jacobsen, Copenhagen Ø (DK); Sari Charlotte Hansen, Skaevinge (DK); Iben Jeppesen, Alleroed (DK)

(73) Assignee: CHR. HANSEN A/S, Hoersholm (DK)

( * ) Notice: Subject to any disclaimer, the term of this patent is extended or adjusted under 35 U.S.C. 154(b) by 434 days.

(21) Appl. No.: 14/402,567

(22) PCT Filed: May 22, 2013

(86) PCT No.: PCT/EP2013/060460
§ 371 (c)(1),
(2) Date: Nov. 20, 2014

(87) PCT Pub. No.: WO2013/174840
PCT Pub. Date: Nov. 28, 2013

(65) Prior Publication Data
US 2015/0173383 A1 Jun. 25, 2015

(30) Foreign Application Priority Data
May 25, 2012 (EP) .................................... 12169503

(51) Int. Cl.
| | | |
|---|---|---|
| C12N 9/64 | (2006.01) | |
| C12N 1/20 | (2006.01) | |
| C12N 15/00 | (2006.01) | |
| C12P 21/06 | (2006.01) | |
| C12P 21/04 | (2006.01) | |
| C07H 21/04 | (2006.01) | |
| A23C 9/12 | (2006.01) | |
| C12N 15/09 | (2006.01) | |
| A23C 11/10 | (2006.01) | |
| A23C 19/032 | (2006.01) | |
| A23C 20/02 | (2006.01) | |
| A23K 20/189 | (2016.01) | |
| C12N 15/52 | (2006.01) | |

(52) U.S. Cl.
CPC .......... *A23C 9/1209* (2013.01); *A23C 11/106* (2013.01); *A23C 19/0326* (2013.01); *A23C 20/025* (2013.01); *A23K 20/189* (2016.05); *C12N 9/6483* (2013.01); *C12N 15/09* (2013.01); *C12Y 304/23004* (2013.01); *C12N 15/52* (2013.01); *C12N 2330/50* (2013.01)

(58) Field of Classification Search
None
See application file for complete search history.

(56) References Cited

U.S. PATENT DOCUMENTS

2017/0067041 A1   3/2017   Van Den Brink et al.

FOREIGN PATENT DOCUMENTS

| WO | WO-02/36752 A2 | 5/2002 |
|---|---|---|
| WO | WO 2008/098973 A1 | 8/2008 |
| WO | WO 2013/164479 A2 | 11/2013 |
| WO | WO 2013/164479 A3 | 11/2013 |
| WO | WO 2013/164481 A1 | 11/2013 |
| WO | WO 2013/174840 A1 | 11/2013 |

OTHER PUBLICATIONS

Branden. Introduction to Protein Structure, Garland Publishing Inc., New York, p. 247, 1991.*
Houen. The primary structure and enzymic properties of porcine prochymosin and chymosin. Int J Biochem Cell Biol. Jun. 1996;28(6):667-75.*
Vallejo. Cloning and expression of buffalo active chymosin in Pichia pastoris. J Agric Food Chem. Nov. 26, 2008;56(22):10606-10.*
Chitpinityol et al., "Site-specific mutations of calf chymosin B which influence milk-clotting activity," Food Chemistry, vol. 62, 1998, pp. 133-139.
International Search Report dated Aug. 11, 2013 issued in PCT/EP2013/060460.
Kappeler et al., "Characterization of recombinant camel chymosin reveals superior properties for the coagulation of bovine and camel milk," Biochemical and Biophysical Research Communications, vol. 342, 2006, pp. 647-654 (available online Feb. 13, 2006).
Pitts et al., "Expression and characterisation of chymosin pH optima mutants produced in *Trichoderma reeseii*" Journal of Biotechnology, vol. 28, 1993, pp. 69-83.
Strop et al., "Engineering Enzyme Subsite Specificity: Preparation, Kinetic Characterization, and X-ray Analysis at 2.0-A Resolution of Va111lPhe Site-Mutated Calf Chymosin," Biochemistry, vol. 29, 1990, pp. 9863-9871.
Suzuki et al., "Alteration of catalytic properties of chymosin by site-directed mutagenesis," Protein Engineering, vol. 2, 1989, pp. 563-569.
Suzuki et al., "Site directed mutagenesis reveals functional contribution of Thr218, Lys220 and Asp304 in chymosin," Protein Engineering, vol. 4, 1990, pp. 69-71.
van den Brink et al., "Increased production of chymosin by glycosylation," Journal of Biotechnology, vol. 125, 2006, pp. 304-310.
Williams et al., "Mutagenesis, biochemical characterization and X-ray structural analysis of point mutants of bovine chymosin," Protein Engineering Design and Selection, vol. 10, 1997, pp. 991-997.
Zhang et al., "Functional implications of disulfide bond, Cys45-Cys50, in recombinant prochymosin," Biochimica et Biophysica Acta, vol. 1343, 1997, pp. 278-286.
Database UniProt [Online] Oct. 1, 2000 (Oct. 1, 2000),"SubName: Full=Prochymosin {ECO:0000313|EMBL:AAF27315.1};", retrieved from EBI accession No. UNIPROT:Q9N1P5 Database accession No. Q9N1P5.

(Continued)

*Primary Examiner* — Yong D Pak
(74) *Attorney, Agent, or Firm* — Foley & Lardner LLP

(57) ABSTRACT

Variants of chymosin with improved milk-clotting properties.

22 Claims, 2 Drawing Sheets

(56) References Cited

OTHER PUBLICATIONS

Figure 2:
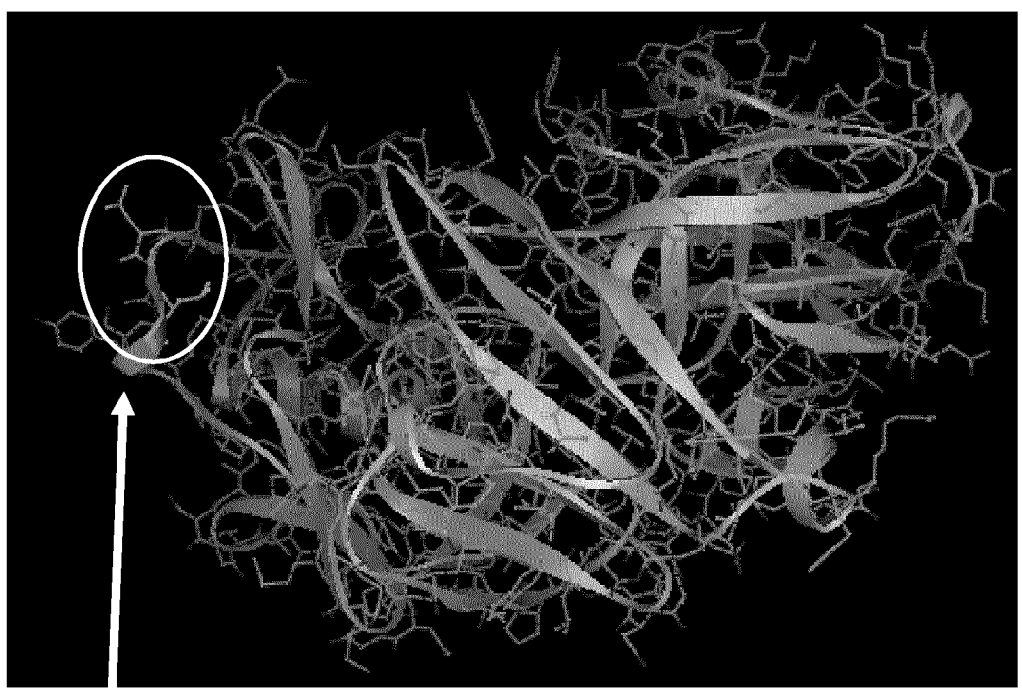

Database UniProt [Online] Feb. 5, 2008 (Feb. 5, 2008), "SubName: Full=Preprochymosin b {ECO:0000313|EMBL:ABX55935.1}; EC=3.4.23.4 {ECO:0000313|EMBL:ABX55935.1};", retrieved from EBI accession No. UNIPROT:A9LY78 Database accession No. A9LY78;—& Juan Andres Vallejo et al: "Cloning and Expression of Buffalo Active Chymosin in Pichia pastoris",Journal of Agricultural and Food Chemistry, vol. 56, No. 22, Nov. 26, 2008 (No. 26, 2008), pp. 10606-10610, XP055004003, ISSN: 0021-8561, DOI: 10.1021/jf802339e.

Database UniProt [Online] Nov. 1, 1990 (Nov. 1, 1990), "RecName: Full=Chymosin; EC=3.4.23.4; AltName: Full=Preprorennin; Flags: Precursor;", retrieved from EBI accession No. UNIPROT:P18276 Database accession No. P18276 ;—& J. Pungercar et al: "Complete primary structure of lamb preprochymosin deduced from cDNA", Nucleic Acids Research, vol. 18, No. 15, Aug. 11, 1990 (Aug. 11, 1990), pp. 4602-4602, XP055314297, GB ISSN: 0305-1048, DOI: 10.1093/nar/18.15.4602.

Database UniProt [Online] Mar. 20, 2007 (Mar. 20, 2007), "SubName: Full=Preprochymosin {ECO:0000313|EMBL:ABN13683.1};", retrieved from EBI accession No. UNIPROT:A3F4M4 Database accession No. A3F4M4.

Database Geneseq [Online] Jan. 2, 2014 (Jan. 2, 2014), "Bovine derived mature chymosin B variant H76Q.", retrieved from EBI accession No. GSP:BAY37837 Database accession No. BAY37837;—& WO 2013/164479 A2 (DSM IP Assets BV [NL]) Nov. 7, 2013 (No. 7, 2013).

Beppu,et al., "Modification of Milk-clotting aspartic proteases, chymosin and mucor rennin," *GBF Monographs*, pp. 87-92 (Dec. 1989).

Preprochymosin b, A9LY78,UniProt, May 16, 2012, [searched on Mar. 17, 2017]. URL: https://www.uniprot.org/A9LY78.txt?version=21.

Kageyama, "New World Monkey Pepsinogens A and C, and Prochymosins, Purification, Characterization of Enzymatic Properties, cDNA Cloning, and Molecular Evolution," *Journal of Biochemistry*, vol. 127, pp. 761-770 (Feb. 2000).

Restriction Requirement issued in co-pending U.S. Appl. No. 15/121,286, dated Jul. 3, 2017 (US 2017/0067041 A1).

Gilliland et al.; "The Three-Dimensional Structure of Recombinant Bovine Chymosin at 2.3 Å Resolution; *Proteins: Structure, Function, and Genetics*"; 8(1): 82-101 (Jan. 1990).

Jensen et al.; "Camel and bovine chymosin: the relationship between their structures and cheese-making properties"; *Acta Crystallographica*; 69(5): 901-913 (May 2013)(published online Apr. 2013).

PCT International Search Report issued in application PCT/EP2015/054020 dated Jul. 6, 2015.

\* cited by examiner

Figure 1

```
                          1                                                    50
Bos_bovis_chymosin_B     MRCLVVLLAV FALSQGAEIT RIPLYKGKSL RKALKEHGLL EDFLQKQQYG
               Sheep    MRCLVVLLAV FALSQGAEIT RIPLYKGKPL RKALKERGLL EDFLQKQQYG
        C._bactrianus    MRCLVVLLAA LALSQASGIT RIPLHKGKTL RKALKERGLL EDFLQRQQYA
   Camelus_dromedarius   MRCLVVLLAA LALSQASGIT RIPLHKGKTL RKALKERGLL EDFLQRQQYA
                 Pig    .IRGRVLLAV LALSQGSGIT RVPLRKGKSL RKELKERGLL EDFLQKQPYA
                 Rat    MRCFVLLLAV LAIAQSHVVT RIPLHKGKSL RNTLKEQGLL EDFLRRHQYE 51                                                   100
Bos_bovis_chymosin_B     ISSKYSGFGE VASVPLTNYL DSQYFGKIYL GTPPQEFTVL FDTGSSDFWV
               Sheep    VSSEYSGFGE VASVPLTNYL DSQYFGKIYL GTPPQEFTVL FDTGSSDFWV
        C._bactrianus    VSSKYSSLGK VAREPLTSYL DSQYFGKIYI GTPPQEFTVV FDTGSSDLWV
   Camelus_dromedarius   VSSKYSSLGK VAREPLTSYL DSQYFGKIYI GTPPQEFTVV FDTGSSDLWV
                 Pig    LSSKYSSFGE VASEPLTNYL DTQYFGKIYI GTPPQEFTVV FDTGSSELWV
                 Rat    FSEKNSNIGM VASEPLTNYL DSEYFGLIYV GTPPQEFKVV FDTGSSELWV 101                                                  150
Bos_bovis_chymosin_B     PSIYCKSNAC KNHQRFDPRK SSTFQNLGKP LSIHYGTGSM QGILGYDTVT
               Sheep    PSIYCKSNAC KNHQRFDPRK SSTFQNLGKP LSIRYGTGSM QGILGYDTVT
        C._bactrianus    PSIYCKSNAC KNHHRFDPRK SSTFRNLGKP LSIHYGTGSI EGFLGYDTVT
   Camelus_dromedarius   PSIYCKSNVC KNHHRFDPRK SSTFRNLGKP LSIHYGTGSM EGFLGYDTVT
                 Pig    PSVYCKSDAC QNHHRFNPSK SSTFQNLDKP LSIQYGTGSI QGFLGYDTVM
                 Rat    PSVYCSSKVC RNHNRFDPSK SFTFQNLSKP LFVQYGTGSV EGFLAYDTVT 151                                                  200
Bos_bovis_chymosin_B     VSNIVDIQQT VGLSTQEPGD VFTYAEFDGI LGMAYPSLAS EYSIPVFDNM
               Sheep    VSNIVDIQQT VGLSTQEPGD VFTYAEFDGI LGMAYPSLAS EYSVPVFDNM
        C._bactrianus    VSNIVDPNQT VGLSTEQPGE VFTYSEFDGI LGLAYPSLAS EYSVPVFDNM
   Camelus_dromedarius   VSNIVDPNQT VGLSTEQPGE VFTYSEFDGI LGLAYPSLAS EYSVPVFDNM
                 Pig    VAGIVDAHQT VGLSTQEPSD IFTYSEFDGI LGLGYPELAS EYTVPVFDNM
                 Rat    VSDIVVPHQT VGLSTEEPGD IFTYSPFDGI LGLAYPTFAS KYSVPIFDNM 201                                                  250
Bos_bovis_chymosin_B     MNRHLVAQDL FSVYMDRNGQ ESMLTLGAID PSYYTGSLHW VPVTVQQYWQ
               Sheep    MDRRLVAQDL FSVYMDRSGQ GSMLTLGAID PSYYTGSLHW VPVTLQKYWQ
        C._bactrianus    MDRHLVARDL FSVYMDRNGQ GSMLTLGATD PSYYTGSLHW VPVTVQQYWQ
   Camelus_dromedarius   MDRHLVARDL FSVYMDRNGQ GSMLTLGAID PSYYTGSLHW VPVTLQQYWQ
                 Pig    MHRHLVAQDL FAVYMSRNDE GSMLTLGAID PSYYTGSLHW VPVTMQLYWQ
                 Rat    MNRHLVAQDL FSVYMSRNDQ GSMLTLGAID QSYFIGSLHW VPVTVQGYWQ 251                                                  300
Bos_bovis_chymosin_B     FTVDSVTISG VVVACEGGCQ AILDTGTSKL VGPSSDILNI QQAIGATQNQ
               Sheep    FTVDSVTISG AVVACEGGCQ AILDTGTSKL VGPSSDILNI QQAIGATQNQ
        C._bactrianus    VTVDSVTING VAVACVGGCQ AILDTGTSVL FGPSSDILKI QMAIGATENR
   Camelus_dromedarius   FTVDSVTING VAVACVGGCQ AILDTGTSVL FGPSSDILKI QMAIGATENR
                 Pig    FTVDSVTING VVVACNGGCQ AILDTGTSML AGPSSDILNI QMAIGATESQ
                 Rat    FTVDRITIND EVVACQGGCP AVLDTGTALL TGPGRDILNI QHAIGAVQGQ 301                                                  350
Bos_bovis_chymosin_B     YGEFDIDCDN LSYMPTVVFE INGKMYPLTP SAYTSQDQGF CTSGFQSENH
               Sheep    YGEFDIDCDS LSSMPTVVFE INGKMYPLTP YAYTSQEEGF CTSGFQGENH
        C._bactrianus    YGEFDVNCGS LRSMPTVVFE INGRDFPLAP SAYTSKDQGF CTSGFQGDNN
   Camelus_dromedarius   YGEFDVNCGN LRSMPTVVFE INGRDYPLSP SAYTSKDQGF CTSGFQGDNN
                 Pig    YGEFDIDCGS LSSMPTVVFE ISGRMYPLPP SAYTNQDQGF CTSGFQGDSK
                 Rat    HDQFDIDCWR LNFMPTVVFE INGREFPLPP SAYTNQFQGS CSSGFR..HG 351                          381
Bos_bovis_chymosin_B     SQKWILGDVF IREYYSVFDR ANNLVGLAKA I
               Sheep    SHQWILGDVF IREYYSVFDR ANNLVGLAKA I
        C._bactrianus    SELWILGDVF IREYYSVFDR ANNRVGLAKA I
   Camelus_dromedarius   SELWILGDVF IREYYSVFDR ANNRVGLAKA I
                 Pig    SQHWILGVVF IQEYYSVFDR ANNRVGLAKA I
                 Rat    SQMWILGDVF IREFYSVFDR ANNRVGLAKA I
```

Positions 296 and 294 in
Bovine Chymosin

US 9,930,899 B2

VARIANTS OF CHYMOSIN WITH IMPROVED MILK-CLOTTING PROPERTIES

CROSS REFERENCE TO RELATED APPLICATIONS

The present application is the U.S. National Stage of International Application No. PCT/EP2013/060460, filed on May 22, 2013, which claims priority to European Patent Application No. 12169503.5, filed on May 25, 2012.

SEQUENCE LISTING

The instant application contains a Sequence Listing which has been submitted electronically in ASCII format and is hereby incorporated by reference in its entirety. Said ASCII copy, created on Aug. 16, 2017, is named 030427-0198_SL.txt and is 20,130 bytes in size.

FIELD OF THE INVENTION

The present invention relates to variants of chymosin with improved milk-clotting properties.

BACKGROUND ART

Enzymatic coagulation of milk by milk-clotting enzymes, such as chymosin and pepsin, is one of the most important processes in the manufacture of cheeses. Enzymatic milk coagulation is a two-phase process: a first phase where a proteolytic enzyme, chymosin or pepsin, attacks κ-casein, resulting in a metastable state of the casein micelle structure and a second phase, where the milk subsequently coagulates and forms a coagulum.

Chymosin (EC 3.4.23.4) and pepsin (EC 3.4.23.1), the milk clotting enzymes of the mammalian stomach, are aspartic proteases belonging to a broad class of peptidases.

When produced in the gastric mucosal cells, chymosin and pepsin occur as enzymatically inactive pre-prochymosin and pre-pepsinogen, respectively. When chymosin is excreted, an N-terminal peptide fragment, the pre-fragment (signal peptide) is cleaved off to give prochymosin including a pro-fragment. Prochymosin is a substantially inactive form of the enzyme which, however, becomes activated under acidic conditions to the active chymosin by autocatalytic removal of the pro-fragment. This activation occurs in vivo in the gastric lumen under appropriate pH conditions or in vitro under acidic conditions.

The structural and functional characteristics of bovine, i.e. *Bos taurus*, pre-prochymosin, prochymosin and chymosin have been studied extensively. The pre-part of the bovine pre-prochymosin molecule comprises 16 aa residues and the pro-part of the corresponding prochymosin has a length of 42 aa residues. The active bovine chymosin comprises 323 aa is a mixture of two forms, A and B, both of which are active.

Chymosin is produced naturally in mammalian species such as bovines, camels, caprines, buffaloes, sheep, pigs, humans, monkeys and rats.

Bovine chymosin has for a number of years been commercially available to the dairy industry.

WO02/36752A2 (Chr. Hansen) describes recombinant production of camel chymosin.

The references listed immediately below may in the present context be seen as references describing mutants of chymosin:

Suzuki et al: Site directed mutagenesis reveals functional contribution of Thr218, Lys220 and Asp304 in chymosin, Protein Engineering, vol. 4, January 1990, pages 69-71;

Suzuki et al: Alteration of catalytic properties of chymosin by site-directed mutagenesis, Protein Engineering, vol. 2, May 1989, pages 563-569;

van den Brink et al: Increased production of chymosin by glycosylation, Journal of biotechnology, vol. 125, September 2006, pages 304-310;

Pitts et al: Expression and characterisation of chymosin pH optima mutants produced in *Tricoderma reesei*, Journal of biotechnology, vol. 28, March 1993, pages 69-83;

M. G. Williams et al: Mutagenesis, biochemical characterization and X-ray structural analysis of point mutants of bovine chymosin, Protein engineering design and selection, vol. 10, September 1997, pages 991-997;

Strop et al: Engineering enzyme subsite specificity: preparation, kinetic characterization, and x-ray analysis at 2.0 ANG resolution of Val111phe site mutated calf chymosin, Biochemistry, vol. 29, October 1990, pages 9863-9871;

Supannee et al: Site-specific mutations of calf chymosin B which influence milk-clotting activity, Food Chemistry, vol. 62, June 1998, pages 133-139;

Zhang et al: Functional implications of disulfide bond, Cys45-Cys50, in recombinant prochymosin, Biochimica et biophysica acta, vol. 1343, December 1997, pages 278-286.

None of the prior art references mentioned above describe directly and unambiguously any of the chymosin mutants/variants as described/claimed below herein.

SUMMARY OF THE INVENTION

The problem to be solved by the present invention is to provide variants of chymosin with improved milk-clotting properties.

As discussed in working examples herein—the present inventors have identified a number of improved camel (see Example 6 herein) and bovine (see Example 7 herein) chymosin variants.

Based on a comparative analysis of the camel and bovine variants—the present inventors identified a number of further amino acid positions that are herein important in the sense that by making a variant in one or more of these positions one may get an improved chymosin variant (see Example 8 herein).

As known in the art—different natural wildtype chymosin polypeptide sequences obtained from different mammalian species (such as e.g. bovines, camels, sheep, pigs, or rats) are having a relatively high sequence similarity/identity.

In FIG. 1 herein this is exemplified by an alignment of herein relevant different chymosin sequences.

In view of this relatively close sequence relation ship—it is believed that the 3D structures of different natural wildtype chymosins are also relatively similar.

In the present context—a natural obtained wildtype chymosin (such as bovine chymosin or camel chymosin) may herein be an example of a parent polypeptide—i.e. a parent polypeptide to which an alteration is made to produce a variant chymosin polypeptide of the present invention.

Without being limited to theory—it is believed that the herein discussed chymosin related amino acid positions are of general importance in any herein relevant chymosin enzyme of interest (e.g. chymosins of e.g. bovines, camels, sheep, pigs, rats etc)—in the sense that by making a variant in one or more of these positions one may get an improved chymosin variant in general (e.g. an improved bovine, camel, sheep, pig or rat chymosin variant).

As discussed herein—as a reference sequence for determining the amino acid position of a parent chymosin polypeptide of interest (e.g. camel, sheep, bovine etc) is herein used the public known bovine chymosin B preprochymosin sequence (Genbank accession number P00794—disclosed as SEQ ID NO: 1 herein).

The bovine chymosin B preprochymosin of SEQ ID NO: 1 may herein alternatively be termed Bovine (*Bos bovis*) chymosin B or simply bovine chymosin. The sequence is also shown in FIG. 1 herein.

Another herein relevant chymosin sequence is publically known *Camelius dromedarius* chymosin sequence of SEQ ID NO: 2 herein. It may herein alternatively be termed camel chymosin. The sequence is also shown in FIG. 1 herein.

In the present context it is believed that a parent chymosin polypeptide (e.g. from sheep or rat) that has at least 65% sequence identity with the mature polypeptide of SEQ ID NO: 1 (bovine chymosin) may herein be seen as sufficient structural related to e.g. bovine or camel chymosin in order to be improved by making a variant in any of the amino acid positions as described herein.

Accordingly, a first aspect of the invention relates to a method for making an isolated chymosin polypeptide variant comprising the steps:

(a): making an alteration at one or more positions in a parent polypeptide having chymosin activity, wherein the alteration is comprising a substitution, a deletion or an insertion in at least one amino acid position corresponding to any of positions 117, 134, 141, 143, 156, 241, 279, 280, 281, 298, 300, 307, 309, 311, 325, 350, 352 and 353; and (b): producing and isolating the altered polypeptide of step (a) and thereby obtaining the isolated chymosin polypeptide variant, wherein the variant has chymosin activity;
and wherein:
(i): the amino acid position of the parent polypeptide is determined by an alignment of the parent polypeptide with the polypeptide of SEQ ID NO: 1 (bovine chymosin)—i.e. the polypeptide of SEQ ID NO: 1 is used to determine the corresponding amino acid sequence in the parent polypeptide; and
(ii): the parent polypeptide has at least 65% sequence identity with the mature polypeptide of SEQ ID NO: 1 (bovine chymosin), which is from amino acid position 59 to amino acid position 381 of SEQ ID NO: 1.

As known in the art—the skilled person may based on his common general knowledge routinely produce and purify chymosin and chymosin variants. Said in other words, once the skilled person is in possession of a herein relevant parent polypeptide having chymosin activity of interest (e.g. from bovines, camels, sheep, pigs, or rats) it is routine work for the skilled person to make a variant of such a parent chymosin of interest.

A second aspect of the invention relates to an isolated chymosin polypeptide variant obtained by the method of first aspect or any herein relevant embodiments thereof.

The term "obtained" in relation to the second aspect above should be understood as that the isolated chymosin polypeptide variant has been obtained by the method of first aspect or any herein relevant embodiments thereof. Accordingly, the term "obtained" in relation to the second aspect should not be understood as obtainable.

As discussed herein—in working examples herein were made variants using the polypeptide of SEQ ID NO: 1 (Bovine) as parent polypeptide—such variant may herein be termed bovine chymosin variants.

Accordingly, a third aspect of the invention relates to an isolated chymosin polypeptide variant comprising:

(a): an alteration at one or more positions in a parent polypeptide having chymosin activity, wherein the alteration is comprising a substitution, a deletion or an insertion in at least one amino acid position corresponding to any of positions 117, 134, 141, 143, 156, 241, 279, 280, 281, 298, 300, 307, 309, 311, 325, 350, 352 and 353; and (b): wherein the variant has chymosin activity;
and wherein:
(i): the amino acid position of the parent polypeptide is determined by an alignment of the parent polypeptide with the polypeptide of SEQ ID NO: 1 (bovine chymosin)—i.e. the polypeptide of SEQ ID NO: 1 is used to determine the corresponding amino acid sequence in the parent polypeptide; and
(ii): the parent polypeptide has at least 90% sequence identity with the mature polypeptide of SEQ ID NO: 1 (bovine chymosin), which is from amino acid position 59 to amino acid position 381 of SEQ ID NO: 1; and
(iii): the isolated variant polypeptide has less than 100% sequence identity with the mature polypeptide of SEQ ID NO: 1 (bovine chymosin).

As discussed herein—in working examples herein were made variants using the polypeptide of SEQ ID NO: 2 (camel chymosin) as parent polypeptide—such variant may herein be termed camel chymosin variant.

Accordingly, a fourth aspect of the invention relates to an isolated chymosin polypeptide variant comprising:

(a): an alteration at one or more positions in a parent polypeptide having chymosin activity, wherein the alteration is comprising a substitution, a deletion or an insertion in at least one amino acid position corresponding to any of positions 117, 134, 141, 143, 156, 241, 279, 280, 281, 298, 300, 307, 309, 311, 325, 350, 352 and 353; and (b): wherein the variant has chymosin activity;
and wherein:
(i): the amino acid position of the parent polypeptide is determined by an alignment of the parent polypeptide with the polypeptide of SEQ ID NO: 1 (bovine chymosin)—i.e. the polypeptide of SEQ ID NO: 1 is used to determine the corresponding amino acid sequence in the parent polypeptide; and
(ii): the parent polypeptide has at least 90% sequence identity with the mature polypeptide of SEQ ID NO: 2 (Camel chymosin), which is from amino acid position 59 to amino acid position 381 of SEQ ID NO: 2; and
(iii): the isolated variant polypeptide has less than 100% sequence identity with the mature polypeptide of SEQ ID NO: 2 (camel chymosin).

An isolated chymosin polypeptide variant as described herein may be used according to the art—e.g. to make a food or feed product of interest (such as e.g. a milk based product of interest that e.g. could be a cheese product).

Accordingly, a fifth aspect of the invention relates to a method for making a food or feed product comprising adding an effective amount of the isolated chymosin polypeptide variant as described herein to the food or feed ingredient(s) and carrying our further manufacturing steps to obtain the food or feed product.

Embodiment of the present invention is described below, by way of examples only.

DEFINITIONS

All definitions of herein relevant terms are in accordance of what would be understood by the skilled person in relation to the herein relevant technical context.

The term "chymosin" relates to an enzyme of the EC 3.4.23.4 class. Chymosin has a high specificity and it clots milk by cleavage of a single 105-Ser-Phe-|-Met-Ala-108 bond in kappa-chain of casein. An alternative name used in the art is rennin.

The term "chymosin activity" relates to chymosin activity of a chymosin enzyme as understood by the skilled person in the present context.

The skilled person knows how to determine herein relevant chymosin activity.

In working Example 4 herein is provided an example of a standard method to determine specific chymosin activity—alternatively termed clotting activity or milk clotting activity.

In working Example 5 herein is provided an example of a standard method to determine proteolytical activity.

As known in the art—the herein relevant so-called C/P ratio is determined by dividing the specific clotting activity (C) with the proteolytical activity (P).

As known in the art—a higher C/P ratio implies generally that the loss of protein during e.g. cheese manufacturing due to non-specific protein degradation is reduced, i.e. the yield of cheese is improved, and that the development of bitter taste in the cheese during maturation is reduced.

The term "isolated variant" means a variant that is modified by the hand of man. In one aspect, the variant is at least 1% pure, e.g., at least 5% pure, at least 10% pure, at least 20% pure, at least 40% pure, at least 60% pure, at least 80% pure, and at least 90% pure, as determined by SDS PAGE.

The term "mature polypeptide" means a peptide in its final form following translation and any post-translational modifications, such as N terminal processing, C terminal truncation, glycosylation, phosphorylation, etc. In the present context may a herein relevant mature chymosin polypeptide be seen as the active chymosin polypeptide sequence—i.e. without the pre-part and/or pro-part sequences. Herein relevant examples of a mature polypeptide are e.g. the mature polypeptide of SEQ ID NO: 1 (bovine chymosin), which is from amino acid position 59 to amino acid position 381 of SEQ ID NO: 1 or the mature polypeptide of SEQ ID NO: 2 (camel chymosin), which is from amino acid position 59 to amino acid position 381 of SEQ ID NO: 2.

The term "parent" or "parent polypeptide having chymosin activity" means a polypeptide to which an alteration is made to produce the enzyme variants of the present invention. The parent may be a naturally occurring (wild-type) polypeptide or a variant thereof.

The term "Sequence Identity" relates to the relatedness between two amino acid sequences or between two nucleotide sequences.

For purposes of the present invention, the degree of sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment–Total Number of Gaps in Alignment)

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

(Identical Deoxyribonucleotides×100)/(Length of Alignment–Total Number of Gaps in Alignment).

The term "variant" means a peptide having chymosin activity comprising an alteration, i.e., a substitution, insertion, and/or deletion, at one or more (several) positions. A substitution means a replacement of an amino acid occupying a position with a different amino acid; a deletion means removal of an amino acid occupying a position; and an insertion means adding 1-3 amino acids adjacent to an amino acid occupying a position.

The amino acid may be natural or unnatural amino acids—for instance, substitution with e.g. a particularly D-isomers (or D-forms) of e.g. D-alanine could theoretically be possible.

The term "wild-type" chymosin peptide means a chymosin expressed by a naturally occurring organism, such as a mammalian (e.g. camel or bovine) found in nature.

DRAWINGS

FIG. 1: An alignment of herein relevant different chymosin sequences. The shown "Bos_bovis_chymosin_B" is bovine chymosin of SEQ ID NO: 1 herein and the shown "Camelus_dromedarius" is camel chymosin of SEQ ID NO: 2 herein. Using bovine chymosin of SEQ ID NO: 1 as reference sequence as described herein is can e.g. be seen that bovine chymosin has "V" in position 10 and camel chymosin has "A" in the same position 10. It may e.g. also be seen that bovine/Rat have "Q" in position 352 and Camel/C._bactrianus have "E" in the same position 352. FIG. 1 discloses SEQ ID NOS 1, 3, 4, 2, 5 and 6, respectively, in order of appearance.

In relation to the chymosin sequences shown in FIG. 1—sheep has 94.5% sequence identity with bovine SEQ ID NO: 1; C._bactrianus has 83.2% sequence identity with bovine SEQ ID NO: 1; Camelus_dromedarius (camel chymosin of SEQ ID NO: 2) has 84% sequence identity with bovine SEQ ID NO: 1; pig has 80.3% sequence identity with bovine SEQ ID NO: 1 and rat has 71.9% sequence with bovine identity SEQ ID NO: 1.

As understood by the skilled person in the present context—herein relevant sequence identity percentages of mature polypeptide sequences of e.g. sheep, C._bactrianus, camel, pig or rat chymosin with the mature polypeptide of SEQ ID NO: 1 (bovine chymosin—i.e. amino acid positions 59 to 381 of SEQ ID NO: 1) are relatively similar to above mentioned sequence identity percentages.

FIG. 2: The 3D structure of bovine chymosin—the 3D structure is public available. As an example are shown where the amino acid positions 296 and 294 are present in bovine Chymosin.

DETAILED DESCRIPTION OF THE INVENTION

Determining the Amino Acid Position of a Chymosin of Interest

As discussed above—as a reference sequence for determining the amino acid position of a herein relevant chymosin polypeptide of interest (e.g. camel, sheep, bovine etc) is herein used the public known bovine chymosin sequence disclosed as SEQ ID NO: 1 herein.

For purposes of the present invention, the polypeptide disclosed in SEQ ID NO: 1 (bovine chymosin) is used to determine the corresponding amino acid residue in another chymosin polypeptide. The amino acid sequence of another chymosin polypeptide is aligned with the polypeptide disclosed in SEQ ID NO: 1, and based on the alignment, the amino acid position number corresponding to any amino acid residue in the polypeptide disclosed in SEQ ID NO: 1 is determined using the ClustalW algorithm as described in working Example 1 herein.

Identification of the corresponding amino acid residue in another chymosin polypeptide can be confirmed by using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later.

Based on above well known computer programs—it is routine work for the skilled person to determine the amino acid position of a herein relevant chymosin polypeptide of interest (e.g. camel, sheep, bovine etc).

In FIG. 1 herein is shown an example of an alignment.

Just as an example—in FIG. 1 can e.g. be seen that herein used bovine reference SEQ ID NO: 1 has a "G" in position 50 and "*Camelus_dromedarius*" (SEQ ID NO: 2 herein) has an "A" in this position 50.

Nomenclature of Variants

In describing the variants of the present invention, the nomenclature described below is adapted for ease of reference. The accepted IUPAC single letter or three letter amino acid abbreviations are employed.

The specific variants discussed in this "nomenclature" section below may not be herein relevant variants of the present invention—i.e. this "nomenclature" section is just to describe the herein relevant used nomenclature as such.

Substitutions.

For an amino acid substitution, the following nomenclature is used: Original amino acid, position, substituted amino acid. Accordingly, a theoretical substitution of threonine with alanine at position 226 is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively. A substitution e.g. designated "226A" refers to a substitution of a parent amino acid (e.g. T, Q, S or another parent amino acid) with alanine at position 226.

Deletions.

For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions.

For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---------|----------|
| 195     | 195 195a 195b |
| G       | G-K-A    |

Multiple Alterations.

Variants comprising multiple alterations are separated by addition marks ("+"), e.g., "Arg170Tyr+Gly195Glu" or "R170Y+G195E" representing a substitution of tyrosine and glutamic acid for arginine and glycine at positions 170 and 195, respectively.

Different Substitutions.

Where different substitutions can be introduced at a position, the different substitutions are separated by a comma, e.g., "Arg170Tyr,Glu" or "R170Y,E" represents a substitution of arginine with tyrosine or glutamic acid at position 170. Thus, "Tyr167Gly,Ala+Arg170Gly,Ala" or "Y167G,A+R170G,A" designates the following variants:

"Tyr167Gly+Arg170Gly", "Tyr167Gly+Arg170Ala", "Tyr167Ala+Arg170Gly", and "Tyr167Ala+Arg170Ala".

A Method for Making an Isolated Chymosin Polypeptide Variant

As discussed above—as known in the art, the skilled person may based on his common general knowledge routinely produce and purify chymosin and chymosin variants.

Said in other words, once the skilled person is in possession of a herein relevant parent polypeptide having chymosin activity of interest (e.g. from bovines, camels, sheep, pigs, or rats) it is routine work for the skilled person to make a variant of such a parent chymosin of interest.

An example of a suitable method to produce and isolate a chymosin (variant or parent) may be by well known e.g. fungal recombinant expression/production based technology as e.g. described in WO02/36752A2 (Chr. Hansen).

It is also routine work for the skilled person to make alteration at one or more positions in a parent polypeptide having chymosin activity, wherein the alteration is comprising a substitution, a deletion or an insertion in at least one amino acid position.

As known to the skilled person—this may e.g. be done by so-called site directed mutagenesis and recombinant expression/production based technology.

It is also routine work for the skilled person to determine if a herein relevant parent polypeptide (e.g. camel or bovine wildtype chymosin) and/or a herein relevant variant has chymosin activity or not.

As known in the art—chymosin activity may be determined by the so-called C/P ratio, which is determined by dividing the specific clotting activity (C) with the proteolytical activity (P).

As known in the art—a higher C/P ratio implies generally that the loss of protein during e.g. cheese manufacturing due to non-specific protein degradation is reduced, i.e. the yield of cheese is improved, and that the development of bitter taste in the cheese during maturation is reduced.

In working example 4 herein is described a suitable method to determine the specific clotting activity (C) and in working example 5 herein is described a suitable method to determine proteolytical activity (P).

Preferably, an isolated chymosin polypeptide variant as described herein is a variant, wherein the variant has a chymosin activity giving a higher C/P ratio as compared to the C/P ratio of bovine chymosin comprising the mature polypeptide of SEQ ID NO: 1 herein.

Preferably, an isolated chymosin polypeptide variant as described herein is a variant, wherein the variant has a chymosin activity giving a higher C/P ratio as compared to the C/P ratio of camel chymosin comprising the mature polypeptide of SEQ ID NO: 2 herein.

More preferably, an isolated chymosin polypeptide variant as described herein is a variant, wherein the variant has
 a chymosin activity giving a higher C/P ratio as compared to the C/P ratio of bovine chymosin comprising the mature polypeptide of SEQ ID NO: 1 herein; and
 a chymosin activity giving a higher C/P ratio as compared to the C/P ratio of camel chymosin comprising the mature polypeptide of SEQ ID NO: 2 herein.

As discussed above—as a reference sequence for determining the amino acid position of a herein relevant chymosin polypeptide of interest (e.g. camel, sheep, bovine etc) is herein used the public known bovine chymosin sequence disclosed as SEQ ID NO: 1 herein.

As discussed above—based on e.g. the computer sequence alignment programs discussed herein—it is routine work for the skilled person to determine the herein relevant amino acid position of a herein relevant chymosin polypeptide of interest (e.g. camel, sheep, bovine etc).

The term "the parent polypeptide has at least 65% sequence identity with the mature polypeptide of SEQ ID NO: 1 (bovine chymosin)" of e.g. the method of the first aspect herein may be seen as relating to a sequence based limitation of the parent chymosin polypeptide used to make a herein relevant variant thereof.

Said in other words—a mature parent chymosin polypeptide (e.g. sheep or pig) that has at least 65% sequence identity with the mature Bovine chymosin is believed to be sufficient structural identical to e.g. Bovine or Camel chymosin in order to be herein relevant—i.e. in the present context it is believed that a mature parent chymosin polypeptide (e.g. from e.g. sheep or rat) that has at least 65% sequence identity with the mature polypeptide of SEQ ID NO: 1 (bovine chymosin) may herein be seen as sufficient structural related to e.g. bovine or camel chymosin in order to be improved by making a variant in any of the amino acid positions as described herein.

The camel chymosin polypeptide of SEQ ID NO: 2 has 84% sequence identity with the bovine polypeptide of SEQ ID NO: 1 (i.e. the complete SEQ ID NO: 1 from position 1 to 381, which includes pre and pro sequence).

As understood by the skilled person in the present context—a herein relevant parent polypeptide having chymosin activity may already e.g. be a variant of e.g. a corresponding wildtype chymosin.

For instance, a camel chymosin variant with e.g. 5-10 alterations (e.g. substitutions) as compared to wildtype camel chymosin polypeptide of SEQ ID NO: 2 will still be a parent polypeptide that has at least 65% sequence identity with the mature polypeptide of SEQ ID NO: 1 (Bovine) as required in e.g. first aspect herein.

Said in other words, a herein relevant isolated chymosin polypeptide variant may comprise alterations (e.g. substitutions) in other position than the positions of e.g. the first aspect herein.

In relation to the chymosin sequences shown in FIG. 1 herein—sheep has 94.5% sequence identity with bovine SEQ ID NO: 1; C._bactrianus has 83.2% sequence identity with bovine SEQ ID NO: 1; pig has 80.3% sequence identity with bovine SEQ ID NO: 1 and rat has 71.9% sequence with bovine identity SEQ ID NO: 1.

As understood by the skilled person in the present context—herein relevant sequence identity percentages of e.g. mature sheep, C._bactrianus, camel, pig or rat chymosin with the mature polypeptide of SEQ ID NO: 1 (bovine chymosin—i.e. amino acid positions 59 to 381 of SEQ ID NO: 1) are relatively similar to above mentioned sequence identity percentages.

Preferred Variants:

As discussed above—e.g. the first aspect relates to an isolated chymosin polypeptide variant, wherein the alteration is comprising a substitution, a deletion or an insertion in at least one amino acid position corresponding to any of positions 117, 134, 141, 143, 156, 241, 279, 280, 281, 298, 300, 307, 309, 311, 325, 350, 352 and 353.

A preferred embodiment relates to an isolated chymosin polypeptide variant, wherein the alteration comprises a substitution, a deletion or an insertion in at least one amino acid position corresponding to any of positions 134, 141, 143, 280, 281, 298, 300, 307, 309, 311, 352 and 353.

It may be preferred that at least one alteration is a substitution—i.e. a herein relevant preferred embodiment relates to an isolated chymosin polypeptide variant, wherein the alteration is comprising a substitution in at least one amino acid position corresponding to any of positions 117, 134, 141, 143, 156, 241, 279, 280, 281, 298, 300, 307, 309, 311, 325, 350, 352 and 353.

Preferably, an isolated chymosin polypeptide variant, wherein the alteration is comprising a substitution in at least one amino acid position corresponding to any of positions 134, 141, 143, 280, 281, 298, 300, 307, 309, 311, 352 and 353.

Preferably, the substitution is wherein the substitution is 117N, 134Q, 141E, 143F, 156V, 241I, 279M, 280I, 281V, 298E, 300R, 307D, 309D, 309W, 311I, 325M, 350N, 352L, 352Q, 353L or 353Q.

As understood by the skilled person in the present context—if the parent chymosin polypeptide already has e.g. "V" in position 156 then is does not make sense to talk about making the substitution 156V for this specific parent chymosin polypeptide. As can be seen in FIG. 1 herein—rat wildtype chymosin has "V" in position 156—the substitution 156V may be seen as herein irrelevant for the specific rat chymosin polypeptide sequence of FIG. 1.

Preferably, the substitution is wherein the substitution is 134Q, 141E, 143F, 280I, 281V, 298E, 300R, 307D, 309D, 309W, 311I, 352L, 352Q, 353L or 353Q.

Preferably, the substitution is wherein the substitution is D117N, H134Q, Q141E, I143F, D156V, V241I, V279M, L280I, F281V, Q298E, Q300R, N307D, G309D, G309W, L311I, D325M, H350N, Q352L, E352L, E352Q, K353L or K353Q.

As understood by the skilled person in the present context—if the parent chymosin polypeptide does not have e.g. "D" in position 156 then is does not make sense to talk about making the substitution D156V for this specific parent chymosin polypeptide. As can be seen in FIG. 1 herein—rat wildtype chymosin has "V" in position 156—the substitution D156V may therefore be seen as herein irrelevant for the specific rat chymosin polypeptide sequence of FIG. 1.

In a preferred embodiment, the substitution is wherein the substitution is H134Q, Q141E, I143F, L280I, F281V, Q298E, Q300R, N307D, G309D, G309W, L311I, Q352L, E352L, E352Q, K353L or K353Q.

In a preferred embodiment, the substitution is wherein the substitution is:

F281V+V306I+I321L;
H134Q+I154L+D216S;
V261A+V263I+G309W+L311I+Y326F;
D156V+G309D+M314L+V317I;
H134Q+L280I+G309W;
R119Q+D156V+V375L;
Y79S+R119S+H204R;
Y79S+H134Q+Y365F+V375L;
Y194I+R213Q+G309D;
Y79S+D117N+I321L;
Y185F+D325M+E352Q;
Y79S+L224V+L311I;
S132F+H134Q+M200I+M215L+G221E;
F281V+G309W+S331Y+D337E;
D156V+G309D+M314L+V317I;
G128D+L188I+Y326F;
R119S+V241I+L280I+L311I+D325M;
R119Q+S284T+T297S+V306I+G309W
K279V+V281F;
Q298E+Q300R;
H350N+Q352E+K353L;
D307N+D309G; or
Q141E+I143F.

Preferred Parent Polypeptide Having Chymosin Activity:

Preferably, the parent polypeptide has at least 70% sequence identity with the mature polypeptide of SEQ ID NO: 1 (bovine chymosin), more preferably the parent polypeptide has at least 75% sequence identity with the mature polypeptide of SEQ ID NO: 1 (bovine chymosin).

Just as an example—a herein suitable relevant parent polypeptide could e.g. be bovine chymosin A—as known in the art bovine chymosin A may only have one amino acid difference as compared to bovine chymosin B of SEQ ID NO: 1 herein.

As discussed above—in working examples herein were made variants using the polypeptide of SEQ ID NO: 1 (Bovine) as parent polypeptide—such variant may herein be termed bovine chymosin variants.

Accordingly, in a preferred embodiment—the parent polypeptide has at least 90% sequence identity with the mature polypeptide of SEQ ID NO: 1 (bovine chymosin), more preferably the parent polypeptide has at least 95% sequence identity with the mature polypeptide of SEQ ID NO: 1 (bovine chymosin) and even more preferably the parent polypeptide has at least 97% sequence identity with the mature polypeptide of SEQ ID NO: 1 (bovine chymosin). It may be preferred that the parent polypeptide is the mature polypeptide of SEQ ID NO: 1 (bovine chymosin).

As understood by the skilled person in the present context—a herein relevant parent polypeptide having chymosin activity may already e.g. be a variant of e.g. a corresponding wildtype chymosin.

For instance, a bovine chymosin variant with e.g. 5-10 alterations (e.g. substitutions) as compared to mature wild-type bovine chymosin polypeptide of SEQ ID NO: 1 will still be a parent polypeptide that has at least 95% sequence identity with the mature polypeptide of SEQ ID NO: 1 (Bovine chymosin).

The mature polypeptide of SEQ ID NO: 1 (Bovine) is 323 amino acids long—accordingly, a bovine chymosin variant with e.g. 25 amino acid substitutions as compared to mature wildtype bovine chymosin polypeptide of SEQ ID NO: 1 will not be a parent polypeptide that has at least 95% sequence identity with the mature polypeptide of SEQ ID NO: 1 (Bovine chymosin).

Said in other words and in general—a herein relevant isolated chymosin polypeptide variant may comprise alterations (e.g. substitutions) in other positions than the positions of e.g. the first aspect herein.

As discussed above—in working examples herein were made variants using the polypeptide of SEQ ID NO: 2 (Camel) as parent polypeptide—such variant may herein be termed camel chymosin variant.

Accordingly, in a preferred embodiment—the parent polypeptide has at least 90% sequence identity with the mature polypeptide of SEQ ID NO: 2 (Camel chymosin), more preferably the parent polypeptide has at least 95% sequence identity with the mature polypeptide of SEQ ID NO: 2 (Camel chymosin) and even more preferably the parent polypeptide has at least 97% sequence identity with the mature polypeptide of SEQ ID NO: 2 (Camel chymosin). It may be preferred that the parent polypeptide is the mature polypeptide of SEQ ID NO: 2 (Camel chymosin).

As understood by the skilled person in the present context—a parent polypeptide that has at least 90% sequence identity with the mature polypeptide of SEQ ID NO: 2 (Camel) is still within the SEQ ID NO: 1 (Bovine) based sequence identity requirement of point (ii) of first aspect herein—i.e. it will be a parent polypeptide that has at least 65% sequence identity with the mature polypeptide of SEQ ID NO: 1 (bovine chymosin).

An Isolated Variant of Bovine Chymosin:

As discussed above—in working examples herein were made variants using the polypeptide of SEQ ID NO: 1 (Bovine) as parent polypeptide—such variant may herein be termed bovine chymosin variants.

As discussed above—the third aspect accordingly relates to an isolated chymosin polypeptide variant comprising:

(a): an alteration at one or more positions in a parent polypeptide having chymosin activity, wherein the alteration is comprising a substitution, a deletion or an insertion in at least one amino acid position corresponding to any of positions 117, 134, 141, 143, 156, 241, 279, 280, 281, 298, 300, 307, 309, 311, 325, 350, 352 and 353; and (b): wherein the variant has chymosin activity;

and wherein:

(i): the amino acid position of the parent polypeptide is determined by an alignment of the parent polypeptide with the polypeptide of SEQ ID NO: 1 (bovine chymosin)—i.e. the polypeptide of SEQ ID NO: 1 is used to determine the corresponding amino acid sequence in the parent polypeptide; and (ii): the parent polypeptide has at least 90% sequence identity with the mature polypeptide of SEQ ID NO: 1 (bovine chymosin), which is from amino acid position 59 to amino acid position 381 of SEQ ID NO: 1; and (iii): the isolated variant polypeptide has less than 100% sequence identity with the mature polypeptide of SEQ ID NO: 1 (bovine chymosin).

The above described definitions and preferred embodiments are also relevant for this aspect.

Preferably, an isolated bovine chymosin polypeptide variant as described herein is a variant, wherein the variant has a chymosin activity giving a higher C/P ratio as compared to the C/P ratio of bovine chymosin comprising the mature polypeptide of SEQ ID NO: 1.

In a preferred embodiment—the parent polypeptide has at least 92% sequence identity with the mature polypeptide of SEQ ID NO: 1 (bovine chymosin), more preferably the parent polypeptide has at least 95% sequence identity with the mature polypeptide of SEQ ID NO: 1 (bovine chymosin) and even more preferably the parent polypeptide has at least 97% sequence identity with the mature polypeptide of SEQ ID NO: 1 (bovine chymosin).

As understood by the skilled person in the present context—an isolated chymosin variant may comprise alterations (e.g. substitutions) in other amino acid positions than given above.

For instance, a bovine chymosin variant with e.g. 5-10 alterations (e.g. substitutions) as compared to wildtype bovine chymosin polypeptide of SEQ ID NO: 1 will still be a parent polypeptide that has at least 95% sequence identity with the mature polypeptide of SEQ ID NO: 1 (Bovine chymosin).

It may be preferred that the isolated bovine chymosin variant comprises less than 30 amino acid alterations (e.g. substitutions) as compared to the mature polypeptide of SEQ ID NO: 1 (bovine chymosin) or it may be preferred that the isolated bovine chymosin variant comprises less than 20 amino acid alterations (e.g. substitutions) as compared to the mature polypeptide of SEQ ID NO: 1 (bovine chymosin) or it may be preferred that the isolated bovine chymosin variant comprises less than 10 amino acid alterations (e.g. substitutions) as compared to the mature polypeptide of SEQ ID NO: 1 (bovine chymosin) or it may be preferred that the isolated bovine chymosin variant comprises less than 5 amino acid alterations (e.g. substitutions) as compared to the mature polypeptide of SEQ ID NO: 1 (bovine chymosin).

As understood by the skilled person in the present context—the term "the isolated variant polypeptide has less than 100% sequence identity with the mature polypeptide of SEQ ID NO: 1 (bovine chymosin)" of point (iii) above relates to that the herein described isolated bovine chymosin variant shall of course not have a polypeptide sequence that is 100% identical to the public known wildtype bovine chymosin sequence of SEQ ID NO: 1.

A preferred embodiment relates to an isolated bovine chymosin polypeptide variant, wherein the alteration comprises a substitution, a deletion or an insertion in at least one amino acid position corresponding to any of positions 134, 141, 143, 280, 281, 298, 300, 307, 309, 311, 352 and 353.

It may be preferred that at least one alteration is a substitution—i.e. a herein relevant preferred embodiment relates to an isolated chymosin polypeptide variant, wherein the alteration is comprising a substitution in at least one amino acid position corresponding to any of positions 117, 134, 141, 143, 156, 241, 279, 280, 281, 298, 300, 307, 309, 311, 325, 350, 352 and 353.

Preferably, an isolated chymosin polypeptide variant, wherein the alteration is comprising a substitution in at least one amino acid position corresponding to any of positions 134, 141, 143, 280, 281, 298, 300, 307, 309, 311, 352 and 353.

Preferably, the substitution is wherein the substitution is 117N, 134Q, 141E, 143F, 156V, 241I, 279M, 280I, 281V, 298E, 300R, 307D, 309D, 309W, 311I, 325M, 350N, 352L, 352Q, 353L or 353Q.

Preferably, the substitution is wherein the substitution is 134Q, 141E, 143F, 280I, 281V, 298E, 300R, 307D, 309D, 309W, 311I, 352L, 352Q, 353L or 353Q.

Preferably, the substitution is wherein the substitution is D117N, H134Q, Q141E, I143F, D156V, V241I, V279M, L280I, F281V, Q298E, Q300R, N307D, G309D, G309W, L311I, D325M, H350N, Q352L, E352L, E352Q, K353L or K353Q.

In a preferred embodiment, the substitution is wherein the substitution is:

F281V+V306I+I321L;
H134Q+I154L+D216S;
V261A+V263I+G309W+L311I+Y326F;
D156V+G309D+M314L+V317I;
H134Q+L280I+G309W;
R119Q+D156V+V375L;
Y79S+R119S+H204R;
Y79S+H134Q+Y365F+V375L;
Y194I+R213Q+G309D;
Y79S+D117N+I321L;
Y185F+D325M+E352Q;
Y79S+L224V+L311I;
S132F+H134Q+M200I+M215L+G221E;
F281V+G309W+S331Y+D337E;
D156V+G309D+M314L+V317I;
G128D+L188I+Y326F;
R119S+V241I+L280I+L311I+D325M;
R119Q+S284T+T297S+V306I+G309W
K279V+V281F;
Q298E+Q300R;
H350N+Q352E+K353L;
D307N+D309G; or
Q141E+I143F.

An Isolated Variant of Camel Chymosin:

As discussed above—in working examples herein were made variants using the polypeptide of SEQ ID NO: 2 (camel chymosin) as parent polypeptide—such variant may herein be termed camel chymosin variant.

As discussed above—the fourth aspect accordingly relates to an isolated chymosin polypeptide variant comprising:

(a): an alteration at one or more positions in a parent polypeptide having chymosin activity, wherein the alteration is comprising a substitution, a deletion or an insertion in at least one amino acid position corresponding to any of positions 117, 134, 141, 143, 156, 241, 279, 280, 281, 298, 300, 307, 309, 311, 325, 350, 352 and 353; and (b): wherein the variant has chymosin activity;

and wherein:

(i): the amino acid position of the parent polypeptide is determined by an alignment of the parent polypeptide with the polypeptide of SEQ ID NO: 1 (bovine chymosin)—i.e. the polypeptide of SEQ ID NO: 1 is used to determine the corresponding amino acid sequence in the parent polypeptide; and (ii): the parent polypeptide has at least 90% sequence identity with the mature polypeptide of SEQ ID NO: 2 (camel chymosin); and (iii): the isolated variant polypeptide has less than 100% sequence identity with the mature polypeptide of SEQ ID NO: 2 (camel chymosin).

The above described definitions and preferred embodiments are also relevant for this aspect.

Preferably, an isolated camel chymosin polypeptide variant as described herein is a variant, wherein the variant has a chymosin activity giving a higher C/P ratio as compared to the C/P ratio of camel chymosin comprising the mature polypeptide of SEQ ID NO: 2.

In a preferred embodiment—the parent polypeptide has at least 92% sequence identity with the mature polypeptide of SEQ ID NO: 2 (camel chymosin), more preferably the parent polypeptide has at least 95% sequence identity with the mature polypeptide of SEQ ID NO: 2 (camel chymosin) and even more preferably the parent polypeptide has at least 97% sequence identity with the mature polypeptide of SEQ ID NO: 2 (camel chymosin).

As understood by the skilled person in the present context—an isolated chymosin variant may comprise alterations (e.g. substitutions) in other amino acid positions than given above.

For instance, a camel chymosin variant with e.g. 5-10 alterations (e.g. substitutions) as compared to wildtype camel chymosin polypeptide of SEQ ID NO: 2 will still be a parent polypeptide that has at least 95% sequence identity with the mature polypeptide of SEQ ID NO: 2 (camel chymosin).

It may be preferred that the isolated camel chymosin variant comprises less than 30 amino acid alterations (e.g. substitutions) as compared to the mature polypeptide of SEQ ID NO: 2 (camel chymosin) or it may be preferred that the isolated camel chymosin variant comprises less than 20 amino acid alterations (e.g. substitutions) as compared to the mature polypeptide of SEQ ID NO: 2 (camel chymosin) or it may be preferred that the isolated camel chymosin variant comprises less than 10 amino acid alterations (e.g. substitutions) as compared to the mature polypeptide of SEQ ID NO: 2 (camel chymosin) or it may be preferred that the isolated camel chymosin variant comprises less than 5 amino acid alterations (e.g. substitutions) as compared to the mature polypeptide of SEQ ID NO: 2 (camel chymosin).

As understood by the skilled person in the present context—the term "the isolated variant polypeptide has less than 100% sequence identity with the mature polypeptide of SEQ ID NO: 2 (camel chymosin)" of point (iii) above relates to that the herein described isolated camel chymosin variant shall of course not have a polypeptide sequence that is 100% identical to the public known wildtype camel chymosin sequence of SEQ ID NO: 2.

A preferred embodiment relates to an isolated camel chymosin polypeptide variant, wherein the alteration comprises a substitution, a deletion or an insertion in at least one amino acid position corresponding to any of positions 134, 141, 143, 280, 281, 298, 300, 307, 309, 311, 352 and 353.

It may be preferred that at least one alteration is a substitution—i.e. a herein relevant preferred embodiment relates to an isolated chymosin polypeptide variant, wherein the alteration is comprising a substitution in at least one amino acid position corresponding to any of positions 117, 134, 141, 143, 156, 241, 279, 280, 281, 298, 300, 307, 309, 311, 325, 350, 352 and 353.

Preferably, an isolated chymosin polypeptide variant, wherein the alteration is comprising a substitution in at least one amino acid position corresponding to any of positions 134, 141, 143, 280, 281, 298, 300, 307, 309, 311, 352 and 353.

Preferably, the substitution is wherein the substitution is 117N, 134Q, 141E, 143F, 156V, 241I, 279M, 280I, 281V, 298E, 300R, 307D, 309D, 309W, 311I, 325M, 350N, 352L, 352Q, 353L or 353Q.

Preferably, the substitution is wherein the substitution is 134Q, 141E, 143F, 280I, 281V, 298E, 300R, 307D, 309D, 309W, 311I, 352L, 352Q, 353L or 353Q.

Preferably, the substitution is wherein the substitution is D117N, H134Q, Q141E, I143F, D156V, V241I, V279M, L280I, F281V, Q298E, Q300R, N307D, G309D, G309W, L311I, D325M, H350N, Q352L, E352L, E352Q, K353L or K353Q.

In a preferred embodiment, the substitution is wherein the substitution is:
F281V+V306I+I321L;
H134Q+I154L+D216S;
V261A+V263I+G309W+L311I+Y326F;
D156V+G309D+M314L+V317I;
H134Q+L280I+G309W;
R119Q+D156V+V375L;
Y79S+R119S+H204R;
Y79S+H134Q+Y365F+V375L;
Y194I+R213Q+G309D;
Y79S+D117N+I321L;
Y185F+D325M+E352Q;
Y79S+L224V+L311I;
S132F+H134Q+M200I+M215L+G221E;
F281V+G309W+S331Y+D337E;
D156V+G309D+M314L+V317I;
G128D+L188I+Y326F;
R119S+V241I+L280I+L311I+D325M;
R119Q+S284T+T297S+V306I+G309W
K279V+V281F;
Q298E+Q300R;
H350N+Q352E+K353L;
D307N+D309G; or
Q141E+I143F.

A Method for Making a Milk Based Product

As discussed above—an isolated chymosin polypeptide variant as described herein may be used according to the art—e.g. to make a milk based product of interest (such as e.g. a cheese product).

As discussed above—an aspect of the invention relates to a method for making a food or feed product comprising adding an effective amount of the isolated chymosin polypeptide variant as described herein to the food or feed ingredient(s) and carrying our further manufacturing steps to obtain the food or feed product.

Preferably, the food or feed product is a milk based product and wherein the method comprises adding an effective amount of the isolated chymosin polypeptide variant as described herein to milk and carrying our further manufacturing steps to obtain the milk based product.

The milk may e.g. be soy milk, sheep milk, goat milk, buffalo milk, yak milk, lama milk, camel milk or cow milk.

The milk based product may e.g. be a fermented milk product, a quark or a cheese.

Aspects/Embodiments Herein—Presented in Claim Format

Herein described aspects and preferred embodiments of the invention may be presented/described in a so-called claim format—this is done below.

1. A method for making an isolated chymosin polypeptide variant comprising the steps:
(a): making an alteration at one or more positions in a parent polypeptide having chymosin activity, wherein the alteration is comprising a substitution, a deletion or an insertion in at least one amino acid position corresponding to any of positions 117, 134, 141, 143, 156, 241, 279, 280, 281, 298, 300, 307, 309, 311, 325, 350, 352 and 353; and (b): producing and isolating the altered polypeptide of step (a) and thereby obtaining the isolated chymosin polypeptide variant, wherein the variant has chymosin activity; and wherein:

(i): the amino acid position of the parent polypeptide is determined by an alignment of the parent polypeptide with the polypeptide of SEQ ID NO: 1 (bovine chymosin)—i.e. the polypeptide of SEQ ID NO: 1 is used to determine the corresponding amino acid sequence in the parent polypeptide; and (ii): the parent polypeptide has at least 65% sequence identity with the mature polypeptide of SEQ ID NO: 1 (bovine chymosin), which is from amino acid position 59 to amino acid position 381 of SEQ ID NO: 1.

2. The method for making an isolated chymosin polypeptide variant of claim 1, wherein the isolated chymosin polypeptide variant has:

a chymosin activity giving a higher C/P ratio as compared to the C/P ratio of bovine chymosin comprising the mature polypeptide of SEQ ID NO: 1; and a chymosin activity giving a higher C/P ratio as compared to the C/P ratio of camel chymosin comprising the mature polypeptide of SEQ ID NO: 2.

3. The method for making an isolated chymosin polypeptide variant of any of the preceding claims, wherein the alteration comprises a substitution, a deletion or an insertion in at least one amino acid position corresponding to any of positions 134, 141, 143, 280, 281, 298, 300, 307, 309, 311, 352 and 353.

4. The method for making an isolated chymosin polypeptide variant of any of the preceding claims, wherein the alteration is comprising a substitution in at least one amino acid position corresponding to any of positions 117, 134, 141, 143, 156, 241, 279, 280, 281, 298, 300, 307, 309, 311, 325, 350, 352 and 353.

5. The method for making an isolated chymosin polypeptide variant of any of the preceding claims, wherein the alteration is comprising a substitution in at least one amino acid position corresponding to any of positions 134, 141, 143, 280, 281, 298, 300, 307, 309, 311, 352 and 353.

6. The method for making an isolated chymosin polypeptide variant of claim 4, wherein the substitution is 117N, 134Q, 141E, 143F, 156V, 241I, 279M, 280I, 281V, 298E, 300R, 307D, 309D, 309W, 311I, 325M, 350N, 352L, 352Q, 353L or 353Q.

7. The method for making an isolated chymosin polypeptide variant of claim 6, wherein the substitution is 134Q, 141E, 143F, 280I, 281V, 298E, 300R, 307D, 309D, 309W, 311I, 352L, 352Q, 353L or 353Q.

8. The method for making an isolated chymosin polypeptide variant of claim 4, wherein the substitution is D117N, H134Q, Q141E, I143F, D156V, V241I, V279M, L280I, F281V, Q298E, Q300R, N307D, G309D, G309W, L311I, D325M, H350N, Q352L, E352L, E352Q, K353L or K353Q.

9. The method for making an isolated chymosin polypeptide variant of claim 8, wherein the substitution is H134Q, Q141E, I143F, L280I, F281V, Q298E, Q300R, N307D, G309D, G309W, L311I, Q352L, E352L, E352Q, K353L or K353Q.

10. The method for making an isolated chymosin polypeptide variant of claim 4, wherein the substitution is:
F281V+V306I+I321L;
H134Q+I154L+D216S;
V261A+V263I+G309W+L311I+Y326F;
D156V+G309D+M314L+V317I;
H134Q+L280I+G309W;
R119Q+D156V+V375L;
Y79S+R119S+H204R;
Y79S+H134Q+Y365F+V375L;
Y194I+R213Q+G309D;
Y79S+D117N+I321L;
Y185F+D325M+E352Q;
Y79S+L224V+L311I;
S132F+H134Q+M200I+M215L+G221E;
F281V+G309W+S331Y+D337E;
D156V+G309D+M314L+V317I;
G128D+L188I+Y326F;
R119S+V241I+L280I+L311I+D325M;
R119Q+S284T+T297S+V306I+G309W
K279V+V281F;
Q298E+Q300R;
H350N+Q352E+K353L;
D307N+D309G; or
Q141E+I143F.

11. The method for making an isolated chymosin polypeptide variant of any of the preceding claims, wherein the parent polypeptide has at least 75% sequence identity with the mature polypeptide of SEQ ID NO: 1 (bovine chymosin).

12. The method for making an isolated chymosin polypeptide variant of claim 11, wherein the parent polypeptide has at least 95% sequence identity with the mature polypeptide of SEQ ID NO: 1 (bovine chymosin).

13. The method for making an isolated chymosin polypeptide variant of any of claims 1 to 10, wherein the parent polypeptide has at least 95% sequence identity with the mature polypeptide of SEQ ID NO: 2 (Camel chymosin), which is from amino acid position 59 to amino acid position 381 of SEQ ID NO: 2.

14. An isolated chymosin polypeptide variant obtained by the method of any of claims 1 to 13.

15. An isolated chymosin polypeptide variant comprising:

(a): an alteration at one or more positions in a parent polypeptide having chymosin activity, wherein the alteration is comprising a substitution, a deletion or an insertion in at least one amino acid position corresponding to any of positions 117, 134, 141, 143, 156, 241, 279, 280, 281, 298, 300, 307, 309, 311, 325, 350, 352 and 353; and (b): wherein the variant has chymosin activity;

and wherein:

(i): the amino acid position of the parent polypeptide is determined by an alignment of the parent polypeptide with the polypeptide of SEQ ID NO: 1 (bovine chymosin)—i.e. the polypeptide of SEQ ID NO: 1 is used to determine the corresponding amino acid sequence in the parent polypeptide; and (ii): the parent polypeptide has at least 90% sequence identity with the mature polypeptide of SEQ ID NO: 1 (bovine chymosin), which is from amino acid position 59 to amino acid position 381 of SEQ ID NO: 1; and (iii): the isolated variant polypeptide has less than 100% sequence identity with the mature polypeptide of SEQ ID NO: 1 (bovine chymosin).

16. The isolated chymosin polypeptide variant of claim 15, wherein the isolated variant has a chymosin activity giving a higher C/P ratio as compared to the C/P ratio of bovine chymosin comprising the mature polypeptide of SEQ ID NO: 1.

17. The isolated chymosin polypeptide variant of any of claims 15 to 16, wherein the parent polypeptide has at least 97% sequence identity with the mature polypeptide of SEQ ID NO: 1 (bovine chymosin).

18. The isolated chymosin polypeptide variant of any of claims 15 to 17, wherein the isolated bovine chymosin variant comprises less than 10 amino acid alterations (e.g. substitutions) as compared to the mature polypeptide of SEQ ID NO: 1 (bovine chymosin).

19. The isolated chymosin polypeptide variant of any of claims 15 to 18, wherein the alteration comprises a substitution, a deletion or an insertion in at least one amino acid position corresponding to any of positions 134, 141, 143, 280, 281, 298, 300, 307, 309, 311, 352 and 353.

20. The isolated chymosin polypeptide variant of any of claims 15 to 19, wherein the alteration is comprising a substitution in at least one amino acid position corresponding to any of positions 117, 134, 141, 143, 156, 241, 279, 280, 281, 298, 300, 307, 309, 311, 325, 350, 352 and 353.

21. The isolated chymosin polypeptide variant of claim 20, wherein the alteration is comprising a substitution in at least one amino acid position corresponding to any of positions 134, 141, 143, 280, 281, 298, 300, 307, 309, 311, 352 and 353.

22. The isolated chymosin polypeptide variant of claim 20, wherein the substitution is 117N, 134Q, 141E, 143F, 156V, 241I, 279M, 280I, 281V, 298E, 300R, 307D, 309D, 309W, 311I, 325M, 350N, 352L, 352Q, 353L or 353Q.

23. The isolated chymosin polypeptide variant of claim 22, wherein the substitution is 134Q, 141E, 143F, 280I, 281V, 298E, 300R, 307D, 309D, 309W, 311I, 352L, 352Q, 353L or 353Q.

24. The isolated chymosin polypeptide variant of claim 22, wherein the substitution is D117N, H134Q, Q141E, I143F, D156V, V241I, V279M, L280I, F281V, Q298E, Q300R, N307D, G309D, G309W, L311I, D325M, H350N, Q352L, E352L, E352Q, K353L or K353Q.

25. The isolated chymosin polypeptide variant of claim 20, wherein the substitution is:
F281V+V306I+I321L;
H134Q+I154L+D216S;
V261A+V263I+G309W+L311I+Y326F;
D156V+G309D+M314L+V317I;
H134Q+L280I+G309W;
R119Q+D156V+V375L;
Y79S+R119S+H204R;
Y79S+H134Q+Y365F+V375L;
Y194I+R213Q+G309D;
Y79S+D117N+I321L;
Y185F+D325M+E352Q;
Y79S+L224V+L311I;
S132F+H134Q+M200I+M215L+G221E;
F281V+G309W+S331Y+D337E;
D156V+G309D+M314L+V317I;
G128D+L188I+Y326F;
R119S+V241I+L280I+L311I+D325M;
R119Q+S284T+T297S+V306I+G309W
K279V+V281F;
Q298E+Q300R;
H350N+Q352E+K353L;
D307N+D309G; or
Q141E+I143F.

26. An isolated chymosin polypeptide variant comprising:
(a): an alteration at one or more positions in a parent polypeptide having chymosin activity, wherein the alteration is comprising a substitution, a deletion or an insertion in at least one amino acid position corresponding to any of positions 117, 134, 141, 143, 156, 241, 279, 280, 281, 298, 300, 307, 309, 311, 325, 350, 352 and 353; and (b): wherein the variant has chymosin activity;
and wherein:
(i): the amino acid position of the parent polypeptide is determined by an alignment of the parent polypeptide with the polypeptide of SEQ ID NO: 1 (bovine chymosin)—i.e. the polypeptide of SEQ ID NO: 1 is used to determine the corresponding amino acid sequence in the parent polypeptide; and
(ii): the parent polypeptide has at least 90% sequence identity with the mature polypeptide of SEQ ID NO: 2 (Camel chymosin), which is from amino acid position 59 to amino acid position 381 of SEQ ID NO: 2; and
(iii): the isolated variant polypeptide has less than 100% sequence identity with the mature polypeptide of SEQ ID NO: 2 (camel chymosin).

27. The isolated chymosin polypeptide variant of claim 26, wherein the isolated variant has a chymosin activity giving a higher C/P ratio as compared to the C/P ratio of camel chymosin comprising the mature polypeptide of SEQ ID NO: 2.

28. The isolated chymosin polypeptide variant of any of claims 26 to 27, wherein the parent polypeptide has at least 97% sequence identity with the mature polypeptide of SEQ ID NO: 2 (camel chymosin).

29. The isolated chymosin polypeptide variant of any of claims 26 to 28, wherein the isolated camel chymosin variant comprises less than 10 amino acid alterations (e.g. substitutions) as compared to the mature polypeptide of SEQ ID NO: 2 (camel chymosin).

30. The isolated chymosin polypeptide variant of any of claims 26 to 29, wherein the alteration comprises a substitution, a deletion or an insertion in at least one amino acid position corresponding to any of positions 134, 141, 143, 280, 281, 298, 300, 307, 309, 311, 352 and 353.

31. The isolated chymosin polypeptide variant of any of claims 26 to 30, wherein the alteration is comprising a substitution in at least one amino acid position corresponding to any of positions 117, 134, 141, 143, 156, 241, 279, 280, 281, 298, 300, 307, 309, 311, 325, 350, 352 and 353.

32. The isolated chymosin polypeptide variant of claim 31, wherein the alteration is comprising a substitution in at least one amino acid position corresponding to any of positions 134, 141, 143, 280, 281, 298, 300, 307, 309, 311, 352 and 353.

33. The isolated chymosin polypeptide variant of claim 31, wherein the substitution is 117N, 134Q, 141E, 143F, 156V, 241I, 279M, 280I, 281V, 298E, 300R, 307D, 309D, 309W, 311I, 325M, 350N, 352L, 352Q, 353L or 353Q.

34. The isolated chymosin polypeptide variant of claim 33, wherein the substitution is 134Q, 141E, 143F, 280I, 281V, 298E, 300R, 307D, 309D, 309W, 311I, 352L, 352Q, 353L or 353Q.

35. The isolated chymosin polypeptide variant of claim 33, wherein the substitution is D117N, H134Q, Q141E, I143F, D156V, V241I, V279M, L280I, F281V, Q298E, Q300R, N307D, G309D, G309W, L311I, D325M, H350N, Q352L, E352L, E352Q, K353L or K353Q.

36. The isolated chymosin polypeptide variant of claim 31, wherein the substitution is:
F281V+V306I+I321L;
H134Q+I154L+D216S;
V261A+V263I+G309W+L311I+Y326F;
D156V+G309D+M314L+V317I;
H134Q+L280I+G309W;
R119Q+D156V+V375L;
Y79S+R119S+H204R;
Y79S+H134Q+Y365F+V375L;

Y194I+R213Q+G309D;

Y79S+D117N+I321L;

Y185F+D325M+E352Q;

Y79S+L224V+L311I;

S132F+H134Q+M200I+M215L+G221E;

F281V+G309W+S331Y+D337E;

D156V+G309D+M314L+V317I;

G128D+L188I+Y326F;

R119S+V241I+L280I+L311I+D325M;

R119Q+S284T+T297S+V306I+G309W

K279V+V281F;

Q298E+Q300R;

H350N+Q352E+K353L;

D307N+D309G; or

Q141E+I143F.

37: A method for making a food or feed product comprising adding an effective amount of the isolated chymosin polypeptide variant according to any of claims 14 to 36 to the food or feed ingredient(s) and carrying our further manufacturing steps to obtain the food or feed product.

38: The method for making a food or feed product of claim 37, wherein the product is a milk based product and wherein the method comprises adding an effective amount of the isolated chymosin polypeptide variant according to any of claims 14 to 36 to milk and carrying our further manufacturing steps to obtain the milk based product.

39: The method for making a milk based product of claim 38, wherein the milk is soy milk, sheep milk, goat milk, buffalo milk, yak milk, lama milk, camel milk or cow milk.

40: The method for making a milk based product of any of claims 38 to 39, wherein the milk based product is a fermented milk product, a quark or a cheese.

EXAMPLES

Example 1: Alignment and Numbering of Chymosin Protein Sequences and Variant Sequences Chymosin protein sequences were aligned using the ClustalW algorithm as provided by the EBI (EBI, tools, multiple sequence alignment, CLUSTALW", http://www.ebi.ac.uk/Tools/msa/clustalw2/) and as described in Larkin M A, Blackshields G, Brown N P, Chenna R, McGettigan P A, McWilliam H, Valentin F, Wallace I M, Wilm A, Lopez R, Thompson J D, Gibson T J, Higgins D G (2007). Bioinformatics 23(21), 2947-2948.

ClustalW2 settings for multiple sequence alignments were Protein weight Matrix=BLOSUM, GAP open=10, GAP EXTENSION=0.05, GAP DISTANCES=8, No End Gaps, ITERATION=none, NUMITER=1, CLUSTERING=NJ As a reference sequence the bovine chymosin B prepro-chymosin was used (Genbank accession number P00794—disclosed herein as SEQ ID NO: 1), where the N-terminal Methionin has number 1 (MRCL . . . ) and the C-terminal Isoleucin (in the protein sequence . . . LAKAI) has number 381. Variants were aligned against the bovine B pre-pro-chymosin and residues were numbered according to the corresponding bovine chymosin residue.

Example 2: Design of Chymosin Variants

Chymosin variants were designed using different strategies.

When there is referred to camel chymosin there is referred to camel chymosin comprising the polypeptide of SEQ ID NO: 2 herein.

Camel chymosin of SEQ ID NO: 2 may be seen as a herein relevant parent polypeptide having chymosin activity used to make camel chymosin variants thereof.

When there is referred to bovine chymosin there is referred to bovine chymosin comprising the polypeptide of SEQ ID NO: 1 herein.

Bovine chymosin of SEQ ID NO: 1 may be seen as a herein relevant parent polypeptide having chymosin activity used to make bovine chymosin variants thereof.

Variants of camel chymosin were designed based on an alignment of a large set of public known aspartic protease sequences having an identity of 25% or more compared to bovine chymosin B.

Variations were generally introduced in hypervariable regions, while conserved regions were not changed. Multiple variations were introduced in each variant construct, ensuring that each single mutation was present in multiple variant constructs (for discussion of results—see example 6 below).

Variants of bovine chymosin were designed based on a comparison of bovine and camel chymosin. Bovine residues were e.g. changed to the camel counterpart (for discussion of results—see example 7 below).

Example 3: Preparation of Chymosin Variant Enzyme Material

All chymosin variants were synthesized as synthetic genes and cloned into a fungal expression vector corresponding essentially to pGAMpR-C (described in WO02/36752A2)

The vectors were transformed into *E. coli* and plasmid DNA was purified using standard molecular biology protocols, known to the person skilled in the art.

The variant plasmids were individually transformed into an *Aspergillus niger* strain and protein was produced essentially as described in WO02/36752A2 and purified using standard chromatography techniques.

As known in the art—the skilled person may based on his common general knowledge produce and purify chymosin and chymosin variants—such as herein described bovine and camel chymosin variants.

Example 4: Determination of Specific Chymosin Activity 4.1 Determination of Clotting Activity Milk clotting activity was determined using the REMCAT method, which is the standard method developed by the International Dairy Federation (IDF method) Milk clotting activity is determined from the time needed for a visible flocculation of a standard milk substrate prepared from a low-heat, low fat milk powder with a calcium chloride solution of 0.5 g per liter (pH 6.5). The clotting time of a rennet sample is compared to that of a reference standard having known milk-clotting activity and having the same enzyme composition by IDF Standard 110B as the sample. Samples and reference standards were measured under identical chemical and physical conditions. Variant samples were adjusted to approximately 3 IMCU/ml using an 84 mM acetic acid pH 5.5 buffer. Hereafter, 200 µl enzyme was added to 10 ml preheated milk (32° C.) in a glass test tube placed in a water bath, capable of maintaining a constant temperature of 32° C.±1° C. under constant stirring.

The total milk-clotting activity (strength) of a rennet was calculated in International Milk-Clotting Units (IMCU) per ml relative to a standard having the same enzyme composition as the sample according to the formula:

$$\text{Strength in } IMCU/\text{ml} = \frac{\text{Sstandard} \times \text{Tstandard} \times \text{Dsample}}{\text{Dstandard} \times \text{Tsample}}$$

Sstandard: The milk-clotting activity of the international reference standard for rennet.
Tstandard: Clotting time in seconds obtained for the standard dilution.
Dsample: Dilution factor for the sample
Dstandard: Dilution factor for the standard
Tsample: Clotting time in seconds obtained for the diluted rennet sample from addition of enzyme to time of flocculation 4.2 Determination of Total Protein Content Total protein content was determined using the Pierce BCA Protein Assay Kit from Thermo Scientific following the instructions of the providers.

4.3 Calculation of Specific Clotting Activity

Specific clotting activity (IMCU/mg total protein) was determined by dividing the clotting activity (IMCU/ml) by the total protein content (mg total protein per ml).

Example 5: Determination of Proteolytic Activity

General proteolytic activity was measured using fluorescently labelled Bodipy-FL casein as a substrate (EnzChek; Molecular Bioprobes, E6638). Casein derivatives heavily labeled with pH-insensitive green-fluorescent Bodipy-FL result in almost complete quenching of the conjugate's fluorescence. Protease catalyzed hydrolysis releases fluorescent Bodipy-FL. This method is very sensitive which was essential for this experiment as CHYMAX M has the lowest general proteolytical activity of all coagulants known to date.

The assay was conducted in a 0.2 M phosphate buffer adjusted to the desired pH at a final substrate concentration of 0.04 mg/ml. Prior to mixing 1 part of substrate with 1 part of enzyme, both prepared in the phosphate buffer, all enzyme variants where normalized to 50 IMCU/ml (according to Example 4). The substrate and enzyme were mixed in a 96-well Nunc Fluoro microtiter plates, sealed and incubated at 32° C. for 60 min. After incubation the sealing was re-moved and the fluorescence recorded in a fluorimeter.

Example 6: Evaluation of Camel Chymosin Variants

For all variants the specific clotting activity (IMCU/mg of total protein) was determined at pH 6.5 according to Example 4. The variants were ranked using the following strategy. The variant with the lowest specific activity got one point, the second lowest two points etc.

The same ranking strategy was done for the C/P ratio. The C/P ratio was determined for all variant at pH 6.5 by dividing the specific clotting activity (IM-CU/mg) with the proteolytical activity.

The total points for each variant using both ranking strategies were determined and a final ranking was done, based on the sum of the points.

As a reference a camel wildtype gene and a bovine wildtype gene were included.

| | | | | | | | |
|---|---|---|---|---|---|---|---|
| H05-3 | 42453 | F281V | V306I | I321L | x | x | 213 |
| G01-1 | 42419 | H134Q | I154L | D216S | x | x | 210 |
| G10-2 | 42492 | V261A | V263I | G309W | L311I | Y326F | 204 |
| A09-2 | 42478 | D156V | G309D | M314L | V317I | x | 203 |
| E01-1 | 42416 | H134Q | L280I | G309W | x | x | 200 |
| G03-2 | 42436 | R119Q | D156V | V375L | x | x | 197 |
| B06-2 | 42455 | Y79S | R119S | H204R | x | x | 195 |
| B09-2 | 42479 | Y79S | H134Q | Y365F | V375L | x | 194 |
| G02-1 | 42427 | Y194I | R213Q | G309D | x | x | 194 |
| G04-1 | 42444 | Y79S | D117N | I321L | x | x | 193 |
| H02-1 | 42428 | Y185F | D325M | E352Q | x | x | 189 |
| A04-2 | 42438 | Y79S | L224V | L311I | x | x | 186 |
| H10-2 | 42493 | S132F | H134Q | M200I | M215L | G221E | 186 |
| H08-1 | 42477 | F281V | G309W | S331Y | D337E | x | 185 |
| A09-2 | 42478 | D156V | G309D | M314L | V317I | x | 184 |
| H01-1 | 42420 | G128D | L188I | Y326F | x | x | 182 |
| G11-1 | 42500 | R119Q | V241I | L280I | L311I | D325M | 181 |
| H11-2 | 42501 | R119Q | S284T | T297S | V306I | G309W | 178 |
| Camel | 42404 | x | x | x | x | x | 174 |
| G08-2 | 42476 | Q246E | G309D | S329P | D337E | x | 174 |
| G06-1 | 42460 | D156V | M215L | V241I | x | x | 170 |
| H09-1 | 42485 | R125Q | G128N | H204R | Q246E | S284T | 168 |
| H07-2 | 42469 | D117N | V263I | L280I | V306I | x | 167 |
| E06-2 | 42458 | G128D | T244S | L311I | x | x | 151 |
| C03-2 | 42431 | V90L | I154L | S335N | x | x | 148 |
| B07-1 | 42463 | V194I | V279M | L280I | S284T | x | 147 |
| A03-2 | 42429 | Y185F | R213Q | Q246E | x | x | 146 |
| E05-2 | 42450 | D117N | S329P | T342S | x | x | 145 |
| H06-2 | 42461 | G128N | R312S | S313Y | Y326F | x | 145 |
| B03-2 | 42430 | R125Q | V279M | M314L | x | x | 143 |
| B10-1 | 42487 | D216S | L224V | V263I | F281V | G309D | 143 |
| F01-1 | 42417 | V90L | R119Q | H204R | x | x | 143 |
| E03-3 | 42433 | H134Q | K289N | G302D | x | x | 142 |
| A02-2 | 42421 | I154L | G221E | V279M | x | x | 136 |
| F07-2 | 42467 | T297S | I321L | D325M | T342S | x | 135 |
| C11-2 | 42496 | G128D | I154L | I258V | D325M | D337E | 132 |
| D02-1 | 42424 | V261A | S331Y | L353K | x | x | 132 |
| A04-2 | 42438 | Y79S | L224V | L311I | x | x | 131 |
| B01-1 | 42413 | N108K | L280I | S313Y | x | x | 131 |
| D12-1 | 42506 | S190A | V279M | S313Y | S331Y | V375L | 130 |
| A09-2 | 42478 | D156V | G309D | M314L | V317I | x | 129 |
| F09-1 | 42483 | V90L | E352Q | R374L | V375L | x | 129 |
| B12-1 | 42504 | N108K | D117N | M215L | M314L | G347S | 128 |
| D11-1 | 42497 | D156V | H204R | V261A | I321L | S329P | 128 |
| F06-2 | 42459 | D117N | V261A | R312S | x | x | 125 |
| H12-1 | 42502 | V90L | L188I | R203Q | L280I | D337E | 124 |
| D04-2 | 42441 | L188I | G221E | Y365F | x | x | 123 |
| E07-2 | 42466 | R119Q | V279K | K289N | D325M | x | 123 |
| C02-2 | 42423 | R119S | R125Q | K289N | x | x | 122 |
| D05-1 | 42449 | R119S | L224V | T297S | x | x | 122 |
| C08-1 | 42472 | F281V | K289N | L311I | S313Y | x | 117 |
| B02-1 | 42422 | S132F | S180A | R203Q | x | x | 115 |

The term "x" denotes no change-i.e. no mutation.

As all variants included multiple mutations, the data of the ranked variants were investigated in more details using statistical methods and 3D structure analysis, to determine the individual amino acid changes that have a positive or negative effect. In this investigation were also evaluated/included the bovine variants discussed in Example 7 below.

The following mutations were identified:

| | | |
|---|---|---|
| D117N | ++ | Backbone lobe |
| H134Q | ++ | Exposed lobe |
| L280I | ++ | In cleft |
| D156V | + | Backbone |
| V241I | + | Backbone |
| D325M | + | Backbone |
| R374L | -- | Backbone |
| K289N | -- | Other side flap |

-continued

| | | |
|---|---|---|
| V279K | -- | In cleft |
| G302D | -- | Flap |
| L353K | - | Cleft entrance |
| L311I | ++ | Bottom of cleft |
| G309W | + | Outside small lobe |
| G309D | + | |
| V279M | + | |

The term "+" refers to a positive amino acid exchange - i.e. "++" is more positive than "+".
The term "−" refers to a negative amino acid exchange - i.e. "−−" is more negative than "−".

The descriptions of the right column of the table relates to where the individual mutations are situated in the 3D structure of bovine chymosin. The 3D structure of bovine chymosin is publicly available. As an example are in FIG. 2 shown where the amino acid positions 296 and 294 are present in bovine Chymosin.

Conclusions:

The results above demonstrate that following mutations in camel chymosin were positive (i.e. with improved C/P ratio as compared to camel wildtype chymosin):

D117N
H134Q
L280I
D156V
V241I
D325M
L311I
G309W
G309D
V279M

Example 7: Evaluation of Bovine Chymosin Variants

Bovine chymosin variants were evaluated based on their C/P ratio at pH 6.5 only.

| | Mutations Bovine -> camel | Proteolytical/ IMCU | Clotting/mg | C/P |
|---|---|---|---|---|
| 3 | K279V, V281F | 127.237 | 37 | 0, 3 |
| 4 | Q298E, Q300R | 59.942 | 241 | 4, 0 |
| 6 | H350N, Q352E, K353L | 106.417 | 191 | 1, 8 |
| 7 | D307N, D309G | 56.349 | 47 | 0, 8 |
| 8 | Q141E, I143F | 91.011 | 176 | 1, 9 |
| Bovine (3327) | None | 124.237 | 157 | 1, 3 |
| Camel (A01) | None | 53.354 | 197 | 3, 7 |

As all variants included multiple mutations and the data of the ranked variants were investigated in more details, using statistical methods and 3D structure analysis, to determine the individual amino acid changes that have a positive or negative effect. In this investigation were also evaluated/included the camel variants discussed in Example 6.

The following positive mutations for bovine chymosin were identified:

| | |
|---|---|
| Q298E | ++ |
| Q300R | ++ |
| H350N | + |
| K353L | + |
| Q141E | + |
| I143F | + |

The term "+" refers to a positive amino acid exchange - i.e. "++" is more positive than "+".
The term "−" refers to a negative amino acid exchange - i.e. "−−" is more negative than "−".

Conclusions:

The results above demonstrate that following mutations in bovine chymosin were positive (i.e. with improved C/P ratio as compared to bovine wildtype chymosin):

Q300R
H350N
K353L
Q141E
I143F

Example 8: Positions for Making Positive Mutation in Chymosin

A comparative evaluation of the results described in examples 6 and 7 results in following data.

Catalytical Cleft Region 279-281

As shown in example 7, the double mutation K279V and V281F in bovine chymosin resulted in a negative effect on the C/P ratio. In camel chymosin the mutation V279K also resulted in a negative result (example 6). Therefore it is conclude that the optimal amino acid at position 281 is a V. It was also observed that the L280I mutation in camel had a positive effect Small Lobe Region 298-300

As shown in example 7, the double mutation Q298E and Q300R in bovine chymosin had a positive effect on the C/P ratio.

Catalytical Cleft Region 350-353

As shown in example 7, the triple mutation H350N, Q352E and K353L in bovine chymosin had a positive effect on the C/P ratio.

In camel chymosin it was observed (example 6) that a L353Q had a positive effect while a L353K had a negative effect.

Small Lobe Region 307-311

As shown in example 7, the double mutation D307N and D309G in bovine chymosin had a negative effect on the C/P ratio.

In camel chymosin G309D and G309W have a positive effect. This implies that the D307N mutation in bovine chymosin is responsible for the negative effect In camel chymosin a L311I mutation was shown to have beneficial effects.

Back Bone Region 134-143

As shown in example 7, the double mutation Q141E and I143F in bovine chymosin had a positive effect on the C/P ratio Changing H134 into Q in camel chymosin was shown to have a beneficial effect

| Position | Preferred amino acids |
|---|---|
| 280 | I |
| 281 | V |
| 298 | E |
| 300 | R |
| 352 | Q (less preferred L) |
| 309 | D or W |
| 307 | D |
| 141 | E |

-continued

| Position | Preferred amino acids |
|---|---|
| 143 | F |
| 353 | Q |
| 352 | Q |
| 311 | I |
| 134 | Q |

REFERENCES

1: WO02/36752A2 (Chr. Hansen)
2: Suzuki et al: Site directed mutagenesis reveals functional contribution of Thr218, Lys220 and Asp304 in chymosin, Protein Engineering, vol. 4, January 1990, pages 69-71
3: Suzuki et al: Alteration of catalytic properties of chymosin by site-directed mutagenesis, Protein Engineering, vol. 2, May 1989, pages 563-569
4: van den Brink et al: Increased production of chymosin by glycosylation, Journal of biotechnology, vol. 125, September 2006, pages 304-310.
5: Pitts et al: Expression and characterisation of chymosin pH optima mutants produced in *Tricoderma reesei*, Journal of biotechnology, vol. 28, March 1993, pages 69-83
6: M. G. Williams et al: Mutagenesis, biochemical characterization and X-ray structural analysis of point mutants of bovine chymosin, Protein engineering design and selection, vol. 10, September 1997, pages 991-997
7: Strop et al: Engineering enzyme subsite specificity: preparation, kinetic characterization, and x-ray analysis at 2.0 ANG resolution of Val111phe site mutated calf chymosin, Biochemistry, vol. 29, October 1990, pages 9863-9871
8: Supannee et al: Site-specific mutations of calf chymosin B which influence milk-clotting activity, Food Chemistry, vol. 62, June 1998, pages 133-139
9: Zhang et al: Functional implications of disulfide bond, Cys45-Cys50, in recombinant prochymosin, Biochimica et biophysica acta, vol. 1343, December 1997, pages 278-286.

The invention claimed is:

1. A method for making an isolated chymosin polypeptide variant comprising:
   (a) producing a chymosin polypeptide variant having an alteration at one or more positions in its amino acid sequence relative to a parent polypeptide having chymosin activity, wherein the parent polypeptide has at least 65% sequence identity with the mature polypeptide from amino acid position 59 to amino acid position 381 of SEQ ID NO: 1 (bovine chymosin), wherein the alteration comprises a substitution at an amino acid position corresponding to position 117 as determined by an alignment of the amino acid sequence of the parent polypeptide with the amino acid sequence of the polypeptide of SEQ ID NO: 1 (bovine chymosin), and
   (b) isolating the polypeptide variant of step (a), thereby obtaining the isolated chymosin polypeptide variant, wherein the variant has fewer than 30 amino acid alterations in the region from amino acid position 59 to amino acid position 381 as compared to the mature polypeptide from amino acid position 59 to amino acid position 381 of SEQ ID NO: 1 (bovine chymosin) or as compared to the mature polypeptide from amino acid position 59 to amino acid position 381 of SEQ ID NO: 2 (Camel chymosin), as determined by an alignment of the amino acid sequence of the variant with the amino acid sequence of SEQ ID NO: 1 or SEQ ID NO:2, respectively, and has chymosin activity.

2. The method of claim 1, wherein the isolated chymosin polypeptide variant has:
   a chymosin activity giving a higher clotting activity to proteolytical activity (C/P) ratio as compared to the C/P ratio of bovine chymosin comprising the mature polypeptide of SEQ ID NO: 1; and
   a chymosin activity giving a higher C/P ratio as compared to the C/P ratio of camel chymosin comprising the mature polypeptide of SEQ ID NO: 2.

3. The method of claim 1, wherein the alteration comprises the amino acid substitution D117N.

4. The method of claim 1 wherein the alteration comprises the amino acid substitutions Y79S, D117N and I321L.

5. The method of claim 1, wherein the parent polypeptide has at least 95% sequence identity with the mature polypeptide of SEQ ID NO: 1 (bovine chymosin).

6. The method of claim 1, wherein the parent polypeptide has at least 95% sequence identity with the mature polypeptide from amino acid position 59 to amino acid position 381 of SEQ ID NO: 2 (Camel chymosin).

7. An isolated chymosin polypeptide variant obtained by a method that comprises:
   (a) producing a chymosin polypeptide variant having an alteration at one or more positions in its amino acid sequence relative to a parent polypeptide having chymosin activity, wherein the parent polypeptide has at least 65% sequence identity with the mature polypeptide from amino acid position 59 to amino acid position 381 of SEQ ID NO: 1 (bovine chymosin), wherein the alteration comprises a substitution at an amino acid position corresponding to position 117 as determined by an alignment of the amino acid sequence of the parent polypeptide with the amino acid sequence of the polypeptide of SEQ ID NO: 1 (bovine chymosin); and
   (b) isolating the polypeptide variant of step (a), thereby obtaining the isolated chymosin polypeptide variant, wherein the variant has fewer than 30 amino acid alterations in the region from amino acid position 59 to amino acid position 381 as compared to the mature polypeptide from amino acid position 59 to amino acid position 381 of SEQ ID NO: 1 (bovine chymosin) or as compared to the mature polypeptide from amino acid position 59 to amino acid position 381 of SEQ ID NO: 2 (Camel chymosin), as determined by an alignment of the amino acid sequence of the variant with the amino acid sequence of SEQ ID NO: 1 or SEQ ID NO:2, respectively, and has chymosin activity.

8. An isolated chymosin polypeptide variant having an alteration at one or more positions in its amino acid sequence relative to a parent polypeptide having chymosin activity, wherein the parent polypeptide has at least 90% sequence identity with the mature polypeptide from amino acid position 59 to amino acid position 381 of SEQ ID NO: 1 (bovine chymosin), wherein the alteration comprises a substitution at an amino acid position corresponding to position 117 as determined by an alignment of the amino acid sequence of the parent polypeptide with the amino acid sequence of the polypeptide of SEQ ID NO: 1 (bovine chymosin), wherein:
  the variant has chymosin activity;
  the variant has less than 100% sequence identity with the mature polypeptide of SEQ ID NO: 1 (bovine chymosin); and
  the variant has fewer than 30 amino acid alterations in the region from amino acid position 59 to amino acid position 381 as compared to the mature polypeptide from amino acid position 59 to amino acid position 381 of SEQ ID NO: 1 (bovine chymosin), as determined by an alignment of the amino acid sequence of the variant with the amino acid sequence of SEQ ID NO: 1.

9. The isolated chymosin polypeptide variant of claim 8, wherein
  the parent polypeptide has at least 97% sequence identity with the mature polypeptide of SEQ ID NO: 1 (bovine chymosin); and
  the isolated chymosin polypeptide variant comprises fewer than 10 amino acid alterations in the region from amino acid position 59 to amino acid position 381 as compared to the mature polypeptide from amino acid position 59 to amino acid position 381 of SEQ ID NO: 1 (bovine chymosin), as determined by an alignment of the amino acid sequence of the variant with the amino acid sequence of SEQ ID NO: 1.

10. The isolated chymosin polypeptide variant of claim 8, wherein the alteration comprises the amino acid substitution D117N.

11. The isolated chymosin polypeptide variant of claim 8, wherein the alteration comprises the amino acid substitutions Y79S, D117N, and I321L.

12. An isolated chymosin polypeptide variant having an alteration at one or more positions in its amino acid sequence relative to a parent polypeptide having chymosin activity, wherein the parent polypeptide has at least 90% sequence identity with the mature polypeptide from amino acid position 59 to amino acid position 381 of SEQ ID NO: 2 (Camel chymosin), wherein the alteration comprises a substitution at an amino acid position corresponding to position 117 as determined by an alignment of the amino acid sequence of the parent polypeptide with the amino acid sequence of the polypeptide of SEQ ID NO: 1 (bovine chymosin), wherein:
  the variant has chymosin activity; and
  the variant has less than 100% sequence identity with the mature polypeptide of SEQ ID NO: 2 (Camel chymosin); and
  the variant has fewer than 30 amino acid alterations in the region from amino acid position 59 to amino acid position 381 as compared to the mature polypeptide from amino acid position 59 to amino acid position 381 of SEQ ID NO: 2 (Camel chymosin), as determined by an alignment of the amino acid sequence of the variant with the amino acid sequence of SEQ ID NO: 2.

13. The isolated chymosin polypeptide variant of claim 12, wherein the alteration comprises the amino acid substitutions Y79S, D117N and I321L.

14. A method for making a milk-based food or feed product comprising adding an effective amount of the isolated chymosin polypeptide variant according to claim 8 to food or feed ingredient(s) comprising milk.

15. The method for making a milk-based food or feed product according to claim 14, wherein the milk is selected from the group consisting of soya milk, sheep milk, goat milk, buffalo milk, yak milk, lama milk, camel milk and cow milk.

16. The method for making a milk-based food or feed product according to claim 14, wherein the milk-based product is a fermented milk product, a quark or a cheese.

17. A method for making a milk-based food or feed product comprising adding an effective amount of the isolated chymosin polypeptide variant according to claim 12 to food or feed ingredient(s) comprising milk.

18. The method for making a milk-based food or feed product according to claim 17, wherein the milk is selected from the group consisting of soya milk, sheep milk, goat milk, buffalo milk, yak milk, lama milk, camel milk and cow milk.

19. The method for making a milk-based food or feed product according to claim 17, wherein the milk-based product is a fermented milk product, a quark or a cheese.

20. The isolated chymosin polypeptide variant of claim 8, wherein variant has a chymosin activity giving a higher clotting activity to proteolytical activity (C/P) ratio as compared to the C/P ratio of bovine chymosin comprising the mature polypeptide of SEQ ID NO: 1.

21. The isolated chymosin polypeptide variant of claim 12, wherein variant has a chymosin activity giving a higher clotting activity to proteolytical activity (C/P) ratio as compared to the C/P ratio of Camel chymosin comprising the mature polypeptide of SEQ ID NO: 2.

22. The isolated chymosin polypeptide variant of claim 12, wherein the alteration comprises the amino acid substitution D117N.

* * * * *

SEQUENCE LISTING

```
<160> NUMBER OF SEQ ID NOS: 6

<210> SEQ ID NO 1
<211> LENGTH: 381
<212> TYPE: PRT
<213> ORGANISM: Bos taurus

<400> SEQUENCE: 1

Met Arg Cys Leu Val Val Leu Leu Ala Val Phe Ala Leu Ser Gln Gly
1               5                   10                  15

Ala Glu Ile Thr Arg Ile Pro Leu Tyr Lys Gly Lys Ser Leu Arg Lys
            20                  25                  30

Ala Leu Lys Glu His Gly Leu Leu Glu Asp Phe Leu Gln Lys Gln Gln
        35                  40                  45

Tyr Gly Ile Ser Ser Lys Tyr Ser Gly Phe Gly Glu Val Ala Ser Val
    50                  55                  60

Pro Leu Thr Asn Tyr Leu Asp Ser Gln Tyr Phe Gly Lys Ile Tyr Leu
65                  70                  75                  80

Gly Thr Pro Pro Gln Glu Phe Thr Val Leu Phe Asp Thr Gly Ser Ser
                85                  90                  95

Asp Phe Trp Val Pro Ser Ile Tyr Cys Lys Ser Asn Ala Cys Lys Asn
            100                 105                 110

His Gln Arg Phe Asp Pro Arg Lys Ser Ser Thr Phe Gln Asn Leu Gly
        115                 120                 125

Lys Pro Leu Ser Ile His Tyr Gly Thr Gly Ser Met Gln Gly Ile Leu
    130                 135                 140

Gly Tyr Asp Thr Val Thr Val Ser Asn Ile Val Asp Ile Gln Gln Thr
145                 150                 155                 160

Val Gly Leu Ser Thr Gln Glu Pro Gly Asp Val Phe Thr Tyr Ala Glu
                165                 170                 175

Phe Asp Gly Ile Leu Gly Met Ala Tyr Pro Ser Leu Ala Ser Glu Tyr
            180                 185                 190

Ser Ile Pro Val Phe Asp Asn Met Met Asn Arg His Leu Val Ala Gln
        195                 200                 205

Asp Leu Phe Ser Val Tyr Met Asp Arg Asn Gly Gln Glu Ser Met Leu
    210                 215                 220
```

```
Thr Leu Gly Ala Ile Asp Pro Ser Tyr Tyr Thr Gly Ser Leu His Trp
225                 230                 235                 240

Val Pro Val Thr Val Gln Gln Tyr Trp Gln Phe Thr Val Asp Ser Val
            245                 250                 255

Thr Ile Ser Gly Val Val Ala Cys Glu Gly Gly Cys Gln Ala Ile
        260                 265                 270

Leu Asp Thr Gly Thr Ser Lys Leu Val Gly Pro Ser Ser Asp Ile Leu
        275                 280                 285

Asn Ile Gln Gln Ala Ile Gly Ala Thr Gln Asn Gln Tyr Gly Glu Phe
        290                 295                 300

Asp Ile Asp Cys Asp Asn Leu Ser Tyr Met Pro Thr Val Val Phe Glu
305                 310                 315                 320

Ile Asn Gly Lys Met Tyr Pro Leu Thr Pro Ser Ala Tyr Thr Ser Gln
                325                 330                 335

Asp Gln Gly Phe Cys Thr Ser Gly Phe Gln Ser Glu Asn His Ser Gln
            340                 345                 350

Lys Trp Ile Leu Gly Asp Val Phe Ile Arg Glu Tyr Tyr Ser Val Phe
            355                 360                 365

Asp Arg Ala Asn Asn Leu Val Gly Leu Ala Lys Ala Ile
        370                 375                 380

<210> SEQ ID NO 2
<211> LENGTH: 381
<212> TYPE: PRT
<213> ORGANISM: Camelus dromedarius

<400> SEQUENCE: 2

Met Arg Cys Leu Val Val Leu Leu Ala Ala Leu Ala Leu Ser Gln Ala
1               5                   10                  15

Ser Gly Ile Thr Arg Ile Pro Leu His Lys Gly Lys Thr Leu Arg Lys
            20                  25                  30

Ala Leu Lys Glu Arg Gly Leu Leu Glu Asp Phe Leu Gln Arg Gln Gln
        35                  40                  45

Tyr Ala Val Ser Ser Lys Tyr Ser Ser Leu Gly Lys Val Ala Arg Glu
    50                  55                  60

Pro Leu Thr Ser Tyr Leu Asp Ser Gln Tyr Phe Gly Lys Ile Tyr Ile
65                  70                  75                  80

Gly Thr Pro Pro Gln Glu Phe Thr Val Val Phe Asp Thr Gly Ser Ser
                85                  90                  95

Asp Leu Trp Val Pro Ser Ile Tyr Cys Lys Ser Asn Val Cys Lys Asn
            100                 105                 110

His His Arg Phe Asp Pro Arg Lys Ser Ser Thr Phe Arg Asn Leu Gly
        115                 120                 125

Lys Pro Leu Ser Ile His Tyr Gly Thr Gly Ser Met Glu Gly Phe Leu
    130                 135                 140

Gly Tyr Asp Thr Val Thr Val Ser Asn Ile Val Asp Pro Asn Gln Thr
145                 150                 155                 160

Val Gly Leu Ser Thr Glu Gln Pro Gly Glu Val Phe Thr Tyr Ser Glu
                165                 170                 175

Phe Asp Gly Ile Leu Gly Leu Ala Tyr Pro Ser Leu Ala Ser Glu Tyr
            180                 185                 190

Ser Val Pro Val Phe Asp Asn Met Met Asp Arg His Leu Val Ala Arg
        195                 200                 205

Asp Leu Phe Ser Val Tyr Met Asp Arg Asn Gly Gln Gly Ser Met Leu
    210                 215                 220
```

```
Thr Leu Gly Ala Ile Asp Pro Ser Tyr Tyr Thr Gly Ser Leu His Trp
225                 230                 235                 240

Val Pro Val Thr Leu Gln Gln Tyr Trp Gln Phe Thr Val Asp Ser Val
            245                 250                 255

Thr Ile Asn Gly Val Ala Val Ala Cys Val Gly Gly Cys Gln Ala Ile
            260                 265                 270

Leu Asp Thr Gly Thr Ser Val Leu Phe Gly Pro Ser Ser Asp Ile Leu
            275                 280                 285

Lys Ile Gln Met Ala Ile Gly Ala Thr Glu Asn Arg Tyr Gly Glu Phe
            290                 295                 300

Asp Val Asn Cys Gly Asn Leu Arg Ser Met Pro Thr Val Phe Glu
305                 310                 315                 320

Ile Asn Gly Arg Asp Tyr Pro Leu Ser Pro Ser Ala Tyr Thr Ser Lys
                325                 330                 335

Asp Gln Gly Phe Cys Thr Ser Gly Phe Gln Gly Asp Asn Asn Ser Glu
                340                 345                 350

Leu Trp Ile Leu Gly Asp Val Phe Ile Arg Glu Tyr Tyr Ser Val Phe
                355                 360                 365

Asp Arg Ala Asn Asn Arg Val Gly Leu Ala Lys Ala Ile
                370                 375                 380

<210> SEQ ID NO 3
<211> LENGTH: 381
<212> TYPE: PRT
<213> ORGANISM: Ovis aries

<400> SEQUENCE: 3

Met Arg Cys Leu Val Val Leu Leu Ala Val Phe Ala Leu Ser Gln Gly
1               5                   10                  15

Ala Glu Ile Thr Arg Ile Pro Leu Tyr Lys Gly Lys Pro Leu Arg Lys
                20                  25                  30

Ala Leu Lys Glu Arg Gly Leu Leu Glu Asp Phe Leu Gln Lys Gln Gln
            35                  40                  45

Tyr Gly Val Ser Ser Glu Tyr Ser Gly Phe Gly Glu Val Ala Ser Val
50                  55                  60

Pro Leu Thr Asn Tyr Leu Asp Ser Gln Tyr Phe Gly Lys Ile Tyr Leu
65                  70                  75                  80

Gly Thr Pro Pro Gln Glu Phe Thr Val Leu Phe Asp Thr Gly Ser Ser
                85                  90                  95

Asp Phe Trp Val Pro Ser Ile Tyr Cys Lys Ser Asn Ala Cys Lys Asn
                100                 105                 110

His Gln Arg Phe Asp Pro Arg Lys Ser Ser Thr Phe Gln Asn Leu Gly
            115                 120                 125

Lys Pro Leu Ser Ile Arg Tyr Gly Thr Gly Ser Met Gln Gly Ile Leu
130                 135                 140

Gly Tyr Asp Thr Val Thr Val Ser Asn Ile Val Asp Ile Gln Gln Thr
145                 150                 155                 160

Val Gly Leu Ser Thr Gln Glu Pro Gly Asp Val Phe Thr Tyr Ala Glu
                165                 170                 175

Phe Asp Gly Ile Leu Gly Met Ala Tyr Pro Ser Leu Ala Ser Glu Tyr
                180                 185                 190

Ser Val Pro Val Phe Asp Asn Met Met Asp Arg Arg Leu Val Ala Gln
            195                 200                 205

Asp Leu Phe Ser Val Tyr Met Asp Arg Ser Gly Gln Gly Ser Met Leu
```

```
            210                 215                 220
Thr Leu Gly Ala Ile Asp Pro Ser Tyr Thr Gly Ser Leu His Trp
225                 230                 235                 240

Val Pro Val Thr Leu Gln Lys Tyr Trp Gln Phe Thr Val Asp Ser Val
                245                 250                 255

Thr Ile Ser Gly Ala Val Ala Cys Glu Gly Gly Cys Gln Ala Ile
                260                 265                 270

Leu Asp Thr Gly Thr Ser Lys Leu Val Gly Pro Ser Ser Asp Ile Leu
                275                 280                 285

Asn Ile Gln Gln Ala Ile Gly Ala Thr Gln Asn Gln Tyr Gly Glu Phe
                290                 295                 300

Asp Ile Asp Cys Asp Ser Leu Ser Ser Met Pro Thr Val Val Phe Glu
305                 310                 315                 320

Ile Asn Gly Lys Met Tyr Pro Leu Thr Pro Tyr Ala Tyr Thr Ser Gln
                325                 330                 335

Glu Glu Gly Phe Cys Thr Ser Gly Phe Gln Gly Glu Asn His Ser His
                340                 345                 350

Gln Trp Ile Leu Gly Asp Val Phe Ile Arg Glu Tyr Tyr Ser Val Phe
                355                 360                 365

Asp Arg Ala Asn Asn Leu Val Gly Leu Ala Lys Ala Ile
                370                 375                 380

<210> SEQ ID NO 4
<211> LENGTH: 381
<212> TYPE: PRT
<213> ORGANISM: Camelus bactrianus

<400> SEQUENCE: 4

Met Arg Cys Leu Val Val Leu Leu Ala Ala Leu Ala Leu Ser Gln Ala
1               5                   10                  15

Ser Gly Ile Thr Arg Ile Pro Leu His Lys Gly Lys Thr Leu Arg Lys
                20                  25                  30

Ala Leu Lys Glu Arg Gly Leu Leu Glu Asp Phe Leu Gln Arg Gln Gln
            35                  40                  45

Tyr Ala Val Ser Ser Lys Tyr Ser Ser Leu Gly Lys Val Ala Arg Glu
50                  55                  60

Pro Leu Thr Ser Tyr Leu Asp Ser Gln Tyr Phe Gly Lys Ile Tyr Ile
65                  70                  75                  80

Gly Thr Pro Pro Gln Glu Phe Thr Val Val Phe Asp Thr Gly Ser Ser
                85                  90                  95

Asp Leu Trp Val Pro Ser Ile Tyr Cys Lys Ser Asn Ala Cys Lys Asn
                100                 105                 110

His His Arg Phe Asp Pro Arg Lys Ser Ser Thr Phe Arg Asn Leu Gly
            115                 120                 125

Lys Pro Leu Ser Ile His Tyr Gly Thr Gly Ser Ile Glu Gly Phe Leu
            130                 135                 140

Gly Tyr Asp Thr Val Thr Val Ser Asn Ile Val Asp Pro Asn Gln Thr
145                 150                 155                 160

Val Gly Leu Ser Thr Glu Gln Pro Gly Glu Val Phe Thr Tyr Ser Glu
                165                 170                 175

Phe Asp Gly Ile Leu Gly Leu Ala Tyr Pro Ser Leu Ala Ser Glu Tyr
                180                 185                 190

Ser Val Pro Val Phe Asp Asn Met Met Asp Arg His Leu Val Ala Arg
            195                 200                 205
```

```
Asp Leu Phe Ser Val Tyr Met Asp Arg Asn Gly Gln Gly Ser Met Leu
    210                 215                 220

Thr Leu Gly Ala Thr Asp Pro Ser Tyr Tyr Thr Gly Ser Leu His Trp
225                 230                 235                 240

Val Pro Val Thr Val Gln Gln Tyr Trp Gln Val Thr Val Asp Ser Val
                245                 250                 255

Thr Ile Asn Gly Val Ala Val Ala Cys Val Gly Gly Cys Gln Ala Ile
                260                 265                 270

Leu Asp Thr Gly Thr Ser Val Leu Phe Gly Pro Ser Ser Asp Ile Leu
                275                 280                 285

Lys Ile Gln Met Ala Ile Gly Ala Thr Glu Asn Arg Tyr Gly Glu Phe
290                 295                 300

Asp Val Asn Cys Gly Ser Leu Arg Ser Met Pro Thr Val Val Phe Glu
305                 310                 315                 320

Ile Asn Gly Arg Asp Phe Pro Leu Ala Pro Ser Ala Tyr Thr Ser Lys
                325                 330                 335

Asp Gln Gly Phe Cys Thr Ser Gly Phe Gln Gly Asp Asn Asn Ser Glu
                340                 345                 350

Leu Trp Ile Leu Gly Asp Val Phe Ile Arg Glu Tyr Tyr Ser Val Phe
                355                 360                 365

Asp Arg Ala Asn Asn Arg Val Gly Leu Ala Lys Ala Ile
370                 375                 380

<210> SEQ ID NO 5
<211> LENGTH: 380
<212> TYPE: PRT
<213> ORGANISM: Sus scrofa

<400> SEQUENCE: 5

Ile Arg Gly Arg Val Leu Leu Ala Val Leu Ala Leu Ser Gln Gly Ser
1               5                   10                  15

Gly Ile Thr Arg Val Pro Leu Arg Lys Gly Lys Ser Leu Arg Lys Glu
                20                  25                  30

Leu Lys Glu Arg Gly Leu Leu Glu Asp Phe Leu Gln Lys Gln Pro Tyr
            35                  40                  45

Ala Leu Ser Ser Lys Tyr Ser Ser Phe Gly Glu Val Ala Ser Glu Pro
50                  55                  60

Leu Thr Asn Tyr Leu Asp Thr Gln Tyr Phe Gly Lys Ile Tyr Ile Gly
65                  70                  75                  80

Thr Pro Pro Gln Glu Phe Thr Val Val Phe Asp Thr Gly Ser Ser Glu
                85                  90                  95

Leu Trp Val Pro Ser Val Tyr Cys Lys Ser Asp Ala Cys Gln Asn His
                100                 105                 110

His Arg Phe Asn Pro Ser Lys Ser Ser Thr Phe Gln Asn Leu Asp Lys
            115                 120                 125

Pro Leu Ser Ile Gln Tyr Gly Thr Gly Ser Ile Gln Gly Phe Leu Gly
130                 135                 140

Tyr Asp Thr Val Met Val Ala Gly Ile Val Asp Ala His Gln Thr Val
145                 150                 155                 160

Gly Leu Ser Thr Gln Glu Pro Ser Asp Ile Phe Thr Tyr Ser Glu Phe
                165                 170                 175

Asp Gly Ile Leu Gly Leu Gly Tyr Pro Glu Leu Ala Ser Glu Tyr Thr
            180                 185                 190

Val Pro Val Phe Asp Asn Met Met His Arg His Leu Val Ala Gln Asp
        195                 200                 205
```

-continued

```
Leu Phe Ala Val Tyr Met Ser Arg Asn Asp Glu Gly Ser Met Leu Thr
    210                 215                 220

Leu Gly Ala Ile Asp Pro Ser Tyr Tyr Thr Gly Ser Leu His Trp Val
225                 230                 235                 240

Pro Val Thr Met Gln Leu Tyr Trp Gln Phe Thr Val Asp Ser Val Thr
                245                 250                 255

Ile Asn Gly Val Val Ala Cys Asn Gly Cys Gln Ala Ile Leu
                260                 265                 270

Asp Thr Gly Thr Ser Met Leu Ala Gly Pro Ser Ser Asp Ile Leu Asn
                275                 280                 285

Ile Gln Met Ala Ile Gly Ala Thr Glu Ser Gln Tyr Gly Glu Phe Asp
    290                 295                 300

Ile Asp Cys Gly Ser Leu Ser Ser Met Pro Thr Val Phe Glu Ile
305                 310                 315                 320

Ser Gly Arg Met Tyr Pro Leu Pro Pro Ser Ala Tyr Thr Asn Gln Asp
                325                 330                 335

Gln Gly Phe Cys Thr Ser Gly Phe Gln Gly Asp Ser Lys Ser Gln His
                340                 345                 350

Trp Ile Leu Gly Val Val Phe Ile Gln Glu Tyr Tyr Ser Val Phe Asp
    355                 360                 365

Arg Ala Asn Asn Arg Val Gly Leu Ala Lys Ala Ile
370                 375                 380

<210> SEQ ID NO 6
<211> LENGTH: 379
<212> TYPE: PRT
<213> ORGANISM: Rattus sp.

<400> SEQUENCE: 6

Met Arg Cys Phe Val Leu Leu Leu Ala Val Leu Ala Ile Ala Gln Ser
1               5                   10                  15

His Val Val Thr Arg Ile Pro Leu His Lys Gly Lys Ser Leu Arg Asn
                20                  25                  30

Thr Leu Lys Glu Gln Gly Leu Leu Glu Asp Phe Leu Arg Arg His Gln
            35                  40                  45

Tyr Glu Phe Ser Glu Lys Asn Ser Asn Ile Gly Met Val Ala Ser Glu
        50                  55                  60

Pro Leu Thr Asn Tyr Leu Asp Ser Glu Tyr Phe Gly Leu Ile Tyr Val
65                  70                  75                  80

Gly Thr Pro Pro Gln Glu Phe Lys Val Val Phe Asp Thr Gly Ser Ser
                85                  90                  95

Glu Leu Trp Val Pro Ser Val Tyr Cys Ser Ser Lys Val Cys Arg Asn
            100                 105                 110

His Asn Arg Phe Asp Pro Ser Lys Ser Phe Thr Phe Gln Asn Leu Ser
        115                 120                 125

Lys Pro Leu Phe Val Gln Tyr Gly Thr Gly Ser Val Glu Gly Phe Leu
    130                 135                 140

Ala Tyr Asp Thr Val Thr Val Ser Asp Ile Val Val Pro His Gln Thr
145                 150                 155                 160

Val Gly Leu Ser Thr Glu Glu Pro Gly Asp Ile Phe Thr Tyr Ser Pro
                165                 170                 175

Phe Asp Gly Ile Leu Gly Leu Ala Tyr Pro Thr Phe Ala Ser Lys Tyr
        180                 185                 190

Ser Val Pro Ile Phe Asp Asn Met Met Asn Arg His Leu Val Ala Gln
```

-continued

```
                195                 200                 205
Asp Leu Phe Ser Val Tyr Met Ser Arg Asn Asp Gln Gly Ser Met Leu
            210                 215                 220

Thr Leu Gly Ala Ile Asp Gln Ser Tyr Phe Ile Gly Ser Leu His Trp
225                 230                 235                 240

Val Pro Val Thr Val Gln Gly Tyr Trp Gln Phe Thr Val Asp Arg Ile
                245                 250                 255

Thr Ile Asn Asp Glu Val Val Ala Cys Gln Gly Gly Cys Pro Ala Val
            260                 265                 270

Leu Asp Thr Gly Thr Ala Leu Leu Thr Gly Pro Gly Arg Asp Ile Leu
            275                 280                 285

Asn Ile Gln His Ala Ile Gly Ala Val Gln Gly Gln His Asp Gln Phe
        290                 295                 300

Asp Ile Asp Cys Trp Arg Leu Asn Phe Met Pro Thr Val Val Phe Glu
305                 310                 315                 320

Ile Asn Gly Arg Glu Phe Pro Leu Pro Pro Ser Ala Tyr Thr Asn Gln
                325                 330                 335

Phe Gln Gly Ser Cys Ser Ser Gly Phe Arg His Gly Ser Gln Met Trp
                340                 345                 350

Ile Leu Gly Asp Val Phe Ile Arg Glu Phe Tyr Ser Val Phe Asp Arg
            355                 360                 365

Ala Asn Asn Arg Val Gly Leu Ala Lys Ala Ile
370                 375
```